(12) United States Patent
Lewis et al.

(10) Patent No.: US 9,556,208 B2
(45) Date of Patent: Jan. 31, 2017

(54) HYDROSILYLATION SYNTHESIS OF HALOALKYLORGANOSILANES USING PEROXIDE PROMOTERS

(71) Applicant: Momentive Performance Materials Inc., Albany, NY (US)

(72) Inventors: Kenrick Martin Lewis, Flushing, NY (US); Jitendra Singh Rathore, Woodbury, MN (US); Andrea Trotto, Termoli (IT); Giuseppe D'Agostino, Petacciato (IT)

(73) Assignee: Momentive Performance Materials Inc., Waterford, NY (US)

( * ) Notice: Subject to any disclaimer, the term of this patent is extended or adjusted under 35 U.S.C. 154(b) by 29 days.

(21) Appl. No.: 13/650,557

(22) Filed: Oct. 12, 2012

(65) Prior Publication Data
US 2014/0107366 A1 Apr. 17, 2014

(51) Int. Cl.
*C07F 7/18* (2006.01)

(52) U.S. Cl.
CPC .............. *C07F 7/1836* (2013.01); *C07F 7/184* (2013.01); *C07F 7/1876* (2013.01); *Y02P 20/582* (2015.11)

(58) Field of Classification Search
USPC .................................................. 556/479, 485
See application file for complete search history.

(56) References Cited

U.S. PATENT DOCUMENTS

| | | |
|---|---|---|
| 3,795,556 A | 3/1974 | Martin |
| 4,061,609 A | 12/1977 | Bobear |
| 4,578,497 A | 3/1986 | Onopchenko et al. |
| 4,658,050 A | 4/1987 | Quirk et al. |
| 4,727,173 A | 2/1988 | Mendicino |
| 5,103,033 A | 4/1992 | Bank |
| 5,359,113 A | 10/1994 | Bank |
| 5,559,264 A | 9/1996 | Bowman et al. |
| 5,616,762 A | 4/1997 | Kropfgans et al. |
| 5,728,858 A | 3/1998 | Lewis et al. |
| 5,783,720 A | 7/1998 | Mendicino et al. |
| 5,986,122 A | 11/1999 | Lewis et al. |
| 6,015,920 A | 1/2000 | Schilling et al. |
| 6,191,297 B1 | 2/2001 | Batz-Sohn et al. |
| 6,872,845 B2 | 3/2005 | Westmeyer et al. |
| 7,429,672 B2 | 9/2008 | Lewis et al. |
| 2004/0176627 A1* | 9/2004 | Westmeyer et al. .......... 556/466 |

FOREIGN PATENT DOCUMENTS

| | | |
|---|---|---|
| JP | 4 1992 225170 B2 | 7/1992 |
| JP | H11199588 A | 7/1999 |
| JP | 2976011 B2 | 9/1999 |
| JP | 8 1996 261232 B2 | 1/2003 |

OTHER PUBLICATIONS

Berkessel; PATAI's Chemistry of Functional Groups, Online © 2009 John Wiley & Sons, Ltd., p. 1-290.*
Faltynek, Robert A., "Transition-Metal Photocatalysis: Rhodium(1)-Promoted Hydrosilation Reactions", Inorganic Chemistry, vol. 20, pp. 1357-1362 (1981).
Licchelli, Maurizio et al., "Catalyzed Hydrosilylation of 2-Methyl-1Buten-3-Yne with Methyldichlorosilane; Promotional Effect Imparted by the Presence of a Different Chlorosilane", Tetrahedron Letters, vol. 28, No. 32, pp. 3719-3722 (1987).
Marciniec, Bogdan et al., "Catalysis of Hydrosilylation of C=C Bonds by Ruthenium Phosphine Complexes", Journal of Organometallic Chemistry, vol. 253, pp. 349-362 (1983).
Alexandrov, Yu. A., "Preparation, Properties and Applications of Organosilicon Peroxides", Journal of Organometallic Chemistry, vol. 238, pp. 1-78 (1982).
Davies, Alwyn G., "Organosilicon Peroxides: Radicals and Rearrangements", Sciencedirect, Tetrahedron 63, pp. 10385-10405 (2007).
Rose, D. et al., "The Blue Solutions of Ruthenium(II) Chloride: a Cluster Anion", Inorg. Phys. Theor., J. of Chem. Soc. (A), pp. 1791-1795 (1970).
Frosin, K. M. et al., "The Reduction of Hydrated Ruthenium(III) Chloride with Zinc in the Presence of Cyclooctadine", Inorganic Chimica Acta, vol. 167, pp. 83-89 (1990).
Tanaka, Masato et al., "Ruthenium Complex-Catalyzed Hydrosilylation of Allyl Chloride with Trimethoxysilane", Journal of Molecular Catalysis, vol. 81, pp. 207-214 (1993).
Calhoun, Audrey D. et al., "Organic Peroxide Assisted Transition Metal Hydrosilylation Catalysis", Transition Met. Chem., vol. 8, pp. 365-368 (1983).
Deschler et al., "3-Chloropropyltrialkoxysilanes—Key Intermediates for the Commercial Production of Organofunctionalized Silanes and Polysiloxanes", Angew. Chem. Int. Ed. Engl. 25 (1986) pp. 236-252.
Z. Belyakova et. al., "Patterns of behaviour in the reactions of hydride silanes with allyl chloride" Journal of General Chemistry of the USSR, vol. 44, No. 11 (1974), pp. 2399-2401.
E. Chernysev et al., "The influence of additives to the Speier catalyst on hydrosilylation of functionalsed alkenes", Russian Chemical Bulletin, vol. 47, No. 7, (Jul. 1998), pp. 1374-1378.
Dickers et al., "Organosilicon Chemistry. Part 24.1 Homogeneous Rhodium-catalysed Hydrosilation of Alkenes and Alkynes: The Role of Oxygen or Hydroperoxides", J.S.C. Dalton (1980), pp. 308-313.
Mair & Hall, "Organic Peroxides", vol. 2, D. Swern (Editor), pp. 579-599, Chapter 4, John Wiley & Sons, NY (1971).
Jarvie et al., "Reactions of Some Organic Peroxides with Triphenylphosphine and Sodium Dialkyl phosphites", J. Polymer Science: Part A-1, vol. 9 (1971), pp. 3105-3114.
Berkessel et al., "Synthetic uses of peroxides", PATAI's Chemistry of Functional Groups, Online 2009, John Wiley & Sons, Ltd., pp. 1-290.

* cited by examiner

*Primary Examiner* — Pancham Bakshi
(74) *Attorney, Agent, or Firm* — James C. Abruzzo

(57) ABSTRACT

This invention is directed to a process for producing a haloorganoalkoxysilane product comprising reacting an olefinic halide, an alkoxysilane, a catalytically effective amount of ruthenium-containing catalyst; and a reaction-promoting effective amount of a peroxy compound, optionally in the presence of an electron-deficient aromatic compound.

26 Claims, 1 Drawing Sheet

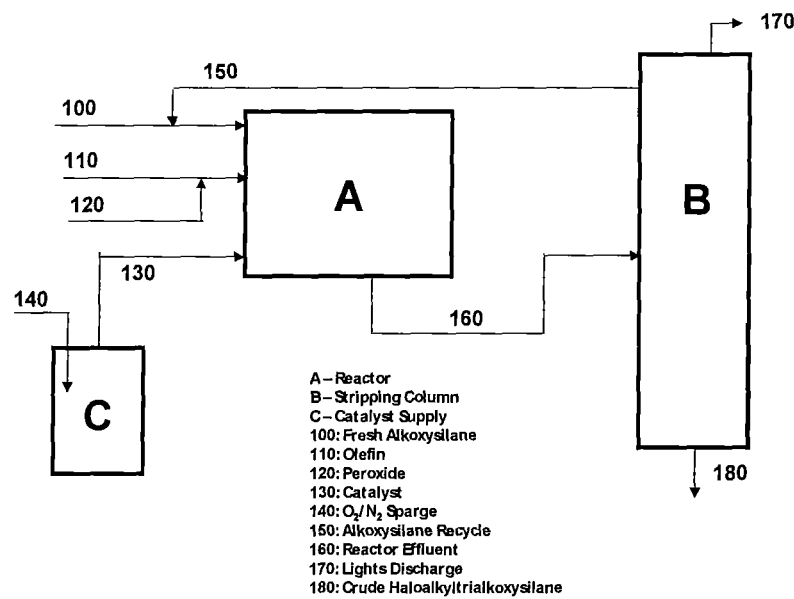
SCHEMATIC OF PEROXIDE PROMOTED HYDROSILYLATION PROCESS
A – Reactor
B – Stripping Column
C – Catalyst Supply
100: Fresh Alkoxysilane
110: Olefin
120: Peroxide
130: Catalyst
140: $O_2/N_2$ Sparge
150: Alkoxysilane Recycle
160: Reactor Effluent
170: Lights Discharge
180: Crude Haloalkyltrialkoxysilane

HYDROSILYLATION SYNTHESIS OF HALOALKYLORGANOSILANES USING PEROXIDE PROMOTERS

FIELD OF THE INVENTION

This invention relates to a process for making haloorganosilicon compounds. More particularly, the invention relates to a process for the preparation of haloorganoalkoxysilanes such as chloropropyltrimethoxysilane and chloropropyltriethoxysilane, via the hydrosilylation of haloalkenes with alkoxysilanes.

BACKGROUND OF THE INVENTION

Chloropropyltrimethoxysilane is a key intermediate for the preparation of a variety of amino-, mercapto- and methacryloyloxyorganosilanes, which are used as silane coupling agents (see Deschler, et al., *Angewandte Chemie, Int. Ed., Engl.*, 25 (1986) 236-252). Chloropropyltrimethoxysilane can also be converted into chloropropyltriethoxysilane, a key intermediate for the preparation of poylsulfane-containing organoalkoxysilanes, which are used in the manufacture of silica-filled tires.

U.S. Pat. No. 6,191,297 discloses a two-step process comprising the ethanol esterification of the product obtained from the platinum-catalyzed hydrosilylation of allyl chloride by trichlorosilane. This process is highly inefficient in its use of material and plant resources due to low yields and significant byproduct formation, namely, propyltrichlorosilane.

A potentially more economical route is the direct hydrosilylation reaction of triethoxysilane and allyl chloride. Large variations in product yield are disclosed in the prior art for the Pt-catalyzed process. According to U.S. Pat. No. 3,795,656, and Japanese Patent 11-199588, the Pt-catalyzed hydrosilylation reaction of allyl chloride and triethoxysilane produces a 70% yield of chloropropyltriethoxy-silane. However, Belyakova, et al., (*Obshch. Khim.*, 44 (1974) 2439-2442) report a 14% yield. Chernyshev, et al. (*Russ. Chem. Bull.* 47(1998) 1374-1378) report a slightly improved yield of 22.7 percent with the use of vinyltriethoxysilane in conjunction with hexachloroplatinic acid.

The primary limitation with the hydrosilylation reaction of allyl chloride and a silane is the competing elimination of propene from allyl chloride. With platinum, the elimination reaction is more prevalent with alkoxysilanes than with chlorosilanes. Rhodium and palladium afford primarily elimination products as depicted in equation (1).

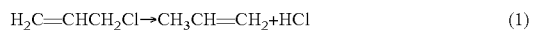

$$H_2C=CHCH_2Cl \rightarrow CH_3CH=CH_2 + HCl \qquad (1)$$

Iridium-containing catalysts have been reported to be very effective for the hydrosilylation reaction of allyl chloride and triethoxysilane. In U.S. Pat. No. 4,658,050, Quirk et al. disclose the iridium-catalyzed hydrosilylation reaction of equimolar quantities of triethoxysilane and allyl chloride with dimeric olefin iridium (I) halide complexes to obtain greater than seventy-five percent yield of 3-chloropropyltriethoxysilane ($Cl(CH_2)_3Si(OC_2H_5)_3$). U.S. Pat. No. 5,616,762 illustrates greater than 80 percent yield of this compound, with minimal byproducts, in an iridium-catalyzed hydrosilylation process wherein the allyl chloride is in stoichiometric excess. Japanese Patent Appl. 4 [1992]-225170 reports similar results for the iridium-catalyzed hydrosilylation reaction of allyl chloride and trimethoxysilane.

Ruthenium and its compounds have been reported to be very efficient catalysts for the hydrosilylation reaction of allyl chloride and trialkoxysilanes. Tanaka, et al., (*J. Mol. Catal.*, 81 (1993) 207-214) report the ruthenium carbonyl-catalyzed hydrosilylation reaction of trimethoxysilane and allyl chloride and Japanese Patent Application 8[1996]-261232 discloses the activation of ruthenium carbonyl for use as a hydrosilylation catalyst for the same reaction. Japanese Patent 2,976,011 discloses the Ru-catalyzed hydrosilylation reaction of triethoxysilane and allyl chloride to give chloropropyltriethoxysilane in about 41% yield. U.S. Pat. No. 5,559,264 describes the hydrosilylation reaction of allyl chloride with a stoichiometric excess of hydridomethoxysilane in the presence of a ruthenium catalyst, and preferably in the substantial absence of solvent, to provide chloropropyltrimethoxysilane. U.S. Pat. No. 6,872,845 discloses an improved hydrosilylation process wherein an electron donating aromatic compound is used as a promoter along with the ruthenium-containing catalyst. Both U.S. patents disclose the optional use of 3% $O_2$ in $N_2$ to activate ruthenium-carbonyl and ruthenium-phosphine catalysts for the subject hydrosilylation.

Marciniec, et al. (*J. Organomet. Chem.*, 253 (1983) 349-362) report the use of Ru(II) and Ru(III) phosphine complexes as catalysts for the hydrosilylation of olefins with trialkoxysilanes. A key teaching is the enhancing effect of molecular oxygen on the desired product formation in reactions catalyzed by Ru(II)-phosphine complexes. The authors theorized that the catalytically active species comprised an Ru(III)-phosphine center bonded to a dioxygen (—O—O—) functionality. The publication states (page 356) that conversion of triethoxysilane can sometimes be as high as 75% in the hydrosilylation of allyl chloride and allylamine with $RuCl_2[(P(C_6H_5)_3]_3$ and $RuCl_3[P(C_6H_5)_3]_3$, but that byproduct formation usually predominates. No information or data was presented on the hydrosilylation of haloalkenes with phosphine-free ruthenium catalysts in the presence of air, oxygen or peroxy compounds.

The beneficial use of molecular oxygen, hydroperoxides and peroxides in some hydrosilylation reactions is known from journal and patent disclosures. Licchelli, et al. (*Tet. Lett.*, 28 (1987) 3719-3722) reported the necessity for benzoyl peroxide in the Pt-catalyzed hydrosilylation of 2-methyl-1-buten-3-yne by methyl dichlorosilane. Alkoxysilanes were not investigated. Benzoyl peroxide usage was 1.64 weight percent of the total weight of reactants. Calhoun, et al., (*Trans. Met. Chem.*, 8(1983) 365-368) found that the catalytic activity of Rh(I)-phosphine complexes for the hydrosilylation of alkenes by alkyl and alkoxysilanes is enhanced by t-butyl hydroperoxide, cumyl hydroperoxide, m-chloroperbenzoic acid, t-butyl perbenzoate and hydrogen peroxide. Optimum product yields depended on the particular combination of metal catalyst and organic peroxy compound. For the hydrosilylation of 1-octene by triethoxysilane, the optimum molar ratio of t-butyl hydroperoxide to Rh was 7.4 for the complex, $RhCl(CO)[P(C_6H_5)_3]_2$. Yields remained approximately constant through molar ratios up to 15.

Calhoun, et al. also investigated the use of Group VIA hexacarbonyls ($M(CO)_6$, M=Cr, Mo, W) in combination with organic peroxides for the hydrosilylation of 2,3-dimethyl-1,3-butadiene by alkyl- and alkoxysilanes. The activities of both $Cr(CO)_6$ and $W(CO)_6$ for formation of the 1-silyl-2,3-dimethyl-2-butene product were enhanced by t-butyl peroxide. Activity of $Mo(CO)_6$ was unaffected by addition of the t-butyl peroxide. Benzoyl peroxide diminished the hydrosilylation activity of $Cr(CO)_6$.

Dickers, et al. (*J. Chem. Soc. Dalton* (1980) 308-313) investigated the hydrosilylation of propene, hex-1-ene and hex-1-yne with triethylsilane catalyzed by Rh(I) and Ir(I) complexed with cycloalkenyl, phosphine, chloride and carbonyl ligands. Reactions catalyzed with phosphine-containing complexes were inhibited, or did not occur, in the absence of oxygen or t-butyl hydroperoxide. With RhCl[P($C_6H_5$)$_3$]$_3$, optimum rates and product yields occurred at molar ratios of t-butyl hydroperoxide to Rh between 1 and 4. Reduced rates and catalyst deactivation were observed at molar ratios greater than 10. Peroxide or oxygen activation was not necessary with the chloro-bridged, cyclooctenyl dimeric Rh(I) complex, [{RhCl($C_8H_{14}$)$_2$}$_2$]. IrCl(CO)[P($C_6H_5$)$_3$]$_2$ remained ineffective even with addition of t-butyl hydroperoxide. Di-t-butyl peroxide was completely ineffective in activating RhCl[P($C_6H_5$)$_3$]$_3$. The authors concluded (page 311) that the beneficial effect of oxygen or hydroperoxide was due to the conversion of the phosphine ligands to phoshine oxides, thereby generating a coordinatively unsaturated center with Rh:P molar ratio ~1. This conclusion also finds support in the data published by Faltynek (*Inorg. Chem.*, 20 (1981) 1357-1362) for photocatalytic hydrosilylations with RhCl[P($C_6H_5$)$_3$]$_3$ in the presence of oxygen and cumeme hydroperoxide.

U.S. Pat. No. 4,578,497 discloses the reactivation of platinum catalysts with oxygen-containing gas to restore hydrosilylation activity with alkyl silanes. The platinum-containing catalyst can be oxygenated prior to use as well as during interruptions in the hydrosilylation process.

U.S. Pat. No. 5,359,113 discloses the use of peroxides and hydroperoxides to maintain catalytic activity in platinum-catalyzed hydrosilylations. Di-t-butyl peroxide, t-butyl hydroperoxide, diacetyl peroxide and dibenzoyl peroxide are examples of the peroxy compounds disclosed. Alkoxysilanes and allyl chloride are included in the list of compounds useful in the invention. 0.05-10 weight percent, preferably 0.1-1 weight percent of the total weight of reactants is disclosed as the effective use range of the peroxides and hydroperoxides in the invention.

U.S. Pat. No. 4,061,609 discloses the advantageous use of hydroperoxides as temporary catalyst inhibitors in silicone rubber compositions cured via platinum-catalyzed hydrosilylation. On the other hand, U.S. Pat. No. 5,986,122 discloses that peroxides and hydroperoxides can inhibit hydrosilylations and claims the use of ascorbic acid and its derivatives to destroy peroxy compounds in allyl polyethers prior to hydrosilylation. Similarly, U.S. Pat. No. 5,103,033 discloses essentially oxygen-free conditions for the hydrosilylation synthesis of β-cyanoalkylsilanes catalyzed by copper-amine complexes.

In summary, the prior art discloses the beneficial use of oxygen and peroxy compounds in some hydrosilylations, but generalizations covering the broad range of transition metal catalysts, unsaturated substrates, hydrido silicon compounds and peroxy compounds are not possible from the available information. In fact, there are hydrosilylations in which oxygen and peroxy compounds are disadvantageous and inhibitive. Ruthenium-containing compounds are known to catalyze hydrosilylations of unsaturated substrates by alkoxysilanes. However, rates and yields are inconsistent for the specific cases of allyl substrates (for example, allyl halides) and alkoxysilanes (for example, triethoxysilane and trimethoxysilane). So in spite of the extensive prior art information, there still exists a need for a reliably consistent ruthenium-catalyzed hydrosilylation process affording high reaction rates and high yields of haloalkylalkoxysilanes from the reaction of allyl halides and alkoxysilanes. The present invention is believed to be an answer to that need.

SUMMARY OF THE INVENTION

In one aspect, the present invention is directed to a process for producing a haloorganoalkoxysilane product of Formula (I), $$(R^1)_y(R^2O)_{3-y}SiCH_2CHR^3CR^4R^5X \qquad (I)$$

comprising reacting (a) an olefinic halide having the formula $H_2C=CR^3CR^4R^5X$; (b) an alkoxysilane having the formula $(R^1)_y(R^2O)_{3-y}SiH$; (c) a catalytically effective amount of ruthenium-containing catalyst; and (d) a reaction-promoting effective amount of a peroxy compound, optionally in the presence of an electron-deficient aromatic compound, to produce the haloorganoalkoxysilane product, wherein $R^1$ and $R^2$ are alkyl groups of from 1 to 6 carbon atoms; $R^3$ is an alkyl group of from 1 to 6 carbon atoms or hydrogen; $R^4$ is an alkyl group of from 1 to 6 carbon atoms, hydrogen or halogen; $R^5$ is hydrogen or an alkyl group of from 1 to 6 carbon atoms; X is a halogen; and y is 0, 1 or 2.

In another aspect, the present invention is directed to a composition produced by the above process comprising a compound of Formula (I), $$(R^1)_y(R^2O)_{3-y}SiCH_2CHR^3CR^4R^5X \qquad (I)$$

and peroxy compounds having 1-2000 ppm peroxy functionality (—O—O—); wherein $R^1$ and $R^2$ are alkyl groups of from 1 to 6 carbon atoms; $R^3$ is an alkyl group of from 1 to 6 carbon atoms or hydrogen; $R^4$ is an alkyl group of from 1 to 6 carbon atoms, hydrogen or halogen; $R^5$ is hydrogen or an alkyl group of from 1 to 6 carbon atoms; X is a halogen; and y is 0, 1 or 2.

BRIEF DESCRIPTION OF THE DRAWING

The invention will be better understood from the following detailed description and examples, taken in conjunction with the drawing, in which:

FIG. 1 is a schematic view of the peroxide-promoted hydrosilylation process of the invention.

DETAILED DESCRIPTION OF THE INVENTION

This invention relates to a process for making haloorganosilicon compounds, and more particularly, to a process for the preparation of haloorganoalkoxysilanes via the hydrosilylation of haloalkenes with alkoxysilanes in the presence of peroxy compounds and a ruthenium catalyst.

By "alkyl" herein is meant to include straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially or deleteriously interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "alkenyl" herein is meant any straight, branched, or cyclic alkenyl group containing one or more carbon-carbon double bonds, where the point of substitution can be either a carbon-carbon double bond or elsewhere in the group. Specific and non-limiting examples of alkenyls include, but are not limited to, vinyl, propenyl, allyl, methallyl, and ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds. In a preferred embodiment, it refers to carbon-carbon double or triple bonds.

By "inert functional group" herein is meant a group other than hydrocarbyl or substituted hydrocarbyl, which is inert under the process conditions to which the compound containing the group is subjected. The inert functional groups also do not substantially or deleteriously interfere with any process described herein that the compound in which they are present may take part in. Examples of inert functional groups include halo (fluoro, chloro, bromo, and iodo), ether such as —$OR^{30}$, wherein $R^{30}$ is hydrocarbyl or substituted hydrocarbyl.

By "hetero atoms" herein is meant any of the Group 13-17 elements except carbon, and can include for example oxygen, nitrogen, silicon, sulfur, phosphorus, fluorine, chlorine, bromine, and iodine.

By "olefin" herein is meant any aliphatic or aromatic hydrocarbon also containing one or more aliphatic carbon-carbon unsaturations. Such olefins may be linear, branched or cyclic and may be substituted with heteroatoms as described above, with the proviso that the substitutents do not interfere substantially or deleteriously with the course of the desired reaction to produce the product.

By "peroxy compound" herein is meant any compound containing a —O—O— moiety.

By "catalytically effective amount" herein is meant an amount effective to catalyze the hydrosilylation reaction.

By "reaction-promoting effective amount" herein is meant an amount sufficient to promote a reaction, but not an amount that will inhibit the reaction.

By "substantially free of phosphine" herein is meant having a phosphine to ruthenium molar ratio of less than $1 \times 10^{-3}$, preferably less than $1 \times 10^{-6}$.

By "halogen" herein is meant any atom that is a member of Group VIIA of the periodic table (fluorine, chlorine, bromine, iodine, astatine). By the prefix "halo" used herein with respect to a compound is meant a compound that contains a halogen atom.

As indicated above, one embodiment of the present invention is directed to a process for producing a haloorganoalkoxysilane product of Formula (I),

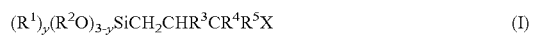   (I)

comprising reacting (a) an olefinic halide having the formula $H_2C{=}CR^3CR^4R^5X$; (b) an alkoxysilane having the formula $(R^1)_y(R^2O)_{3-y}SiH$; (c) a catalytically effective amount of ruthenium-containing catalyst; and (d) a reaction-promoting effective amount of a peroxy compound, optionally in the presence of an electron-deficient aromatic compound, to produce the haloorganoalkoxysilane product, wherein $R^1$ and $R^2$ are alkyl groups of from 1 to 6 carbon atoms; $R^3$ is an alkyl group of from 1 to 6 carbon atoms or hydrogen; $R^4$ is an alkyl group of from 1 to 6 carbon atoms, hydrogen or halogen; $R^5$ is hydrogen or an alkyl group of from 1 to 6 carbon atoms; X is a halogen; and y is 0, 1 or 2.

The principal products of the hydrosilylation process of this invention are haloorganoalkoxysilanes with the general Formula (I)

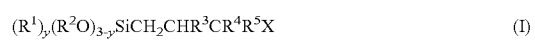   (I)

wherein $R^1$ and $R^2$ are alkyl groups of from 1 to 6 carbon atoms; $R^3$ is an alkyl group of from 1 to 6 carbon atoms or hydrogen; $R^4$ is an alkyl group of from 1 to 6 carbon atoms, hydrogen or halogen; $R^5$ is hydrogen or an alkyl group of from 1 to 6 carbon atoms; X is a halogen; and y is 0, 1 or 2. Specific examples of useful products of the process of the invention include, but are not limited to, $(CH_3O)_3Si(CH_2)_3Cl$, $(C_2H_5O)_3Si(CH_2)_3Cl$, $(C_2H_5O)_3SiCH_2CH(CH_3)CH_2Br$, $(CH_3O)_3SiCH_2CH(Cl)CH_3$, $CH_3(CH_3O)_2Si(CH_2)_2Cl$, and $(C_3H_7O)_3Si(CH_2)_2CH(Cl)CH_3$. Byproducts with the following general formulae are formed during the hydrosilylation reaction $(R^2O)_4Si$, $(R^1)Si(R^2O)_3$, $(R^1)SiH_2(R^2O)$, $(R^2O)_3SiX$, ($R^1$ is not hydrogen)

$(R^2O)_3SiCH_2CHR^3CR^4R^5H$, 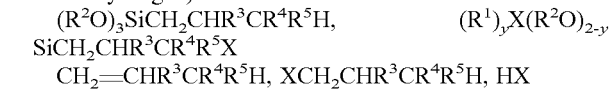

$CH_2{=}CHR^3CR^4R^5H$, $XCH_2CHR^3CR^4R^5H$, HX

Except as indicated above for $R^1$ in $(R^1)Si(R^2O)_3$ and $(R^1)SiH_2(R^2O)$, $R^1$, $R^2$, $R^3$, $R^4$, $R^5$ and X have the same aforestated definitions.

It has been found that several factors are important for obtaining high yields of haloorganoalkoxysilanes from a one-step hydrosilylation reaction between an olefinic halide and an alkoxysilane in the presence of a ruthenium-containing catalyst. Six are emphasized here. First, when all reactants are combined at the start in a batch reaction, selectivity to the desired haloorganoalkoxysilane is highest at lower temperatures and lower reaction rates. Second, when temperature is increased to improve reaction rates, high selectivity can be maintained by limiting the concentration of olefinic halide in the reaction mixture. Third, irrespective of the presence of aromatic compounds, peroxy compounds are required for the maintenance of desirably high activity, high selectivity and reaction stability during the synthesis of the haloorganoalkoxysilanes, especially in a continuous process. Fourth, maintenance of a supply of oxygen to the ruthenium-containing catalyst and/or to the hydrosilylation reaction mixture contributes to high rate, selectivity and stability quite apart from the effects attributable to the peroxy compounds. Fifth, reduction of commercial ruthenium (III) chloride with metallic zinc affords an effective catalyst for hydrosilylation of allyl chloride with trimethoxysilane in the presence of peroxy compounds. Sixth, most inert solvents, and particularly aromatic solvents, when employed at the relatively high levels that are typical for reaction solvents may have deleterious effect on rates, selectivities, or both, particularly in a batch system.

Olefinic Halides

Olefinic halides, which are suitable for use in the present invention, include allyl chloride, methallyl chloride, 3-chloro-1-butene, 3,4-dichloro-1-butene, 2-chloropropene, and the like. Of these, allyl chloride, $H_2C=CHCH_2Cl$, is preferred.

Alkoxysilanes

Alkoxysilanes that are suitable for use in the present invention include trimethoxysilane, methyldimethoxysilane, dimethylmethoxysilane, triethoxysilane, methyldiethoxysilane, dimethylethoxysilane, ethyldiethoxysilane, diethylethoxysilane, and the like. Of these alkoxysilanes, trimethoxysilane and triethoxysilane are preferred.

Peroxy Compounds

Peroxy compounds contain an O—O bond. They are decomposed by heat, acids and some metal compounds. Accordingly, since hydrosilylation processes can be subject to these varied conditions during reaction, product recovery and recycle of unreacted starting materials and catalysts, peroxide promoters must be chosen to sustain stable hydrosilylation activity throughout a batch or continuous process. The term, half-life time ($t_{1/2}$), is customarily used to denote the decomposition behavior of a peroxy compound. Half-life time is the time taken, at a constant temperature, for a peroxy compound to decompose to half of its original amount. It is dependent on solvent polarity and viscosity and the molecular structure of the peroxy compound. A related parameter, which is useful for comparing decomposition rates of the peroxy compounds, is the temperature ($T_{1/2}$, 1 h) at which the half-life time is one hour. Thus, in addition to promoting the hydrosilylation, suitable peroxy compounds must have ($T_{1/2}$, 1 h) values that permit sustained effectiveness and reaction stability. In general, peroxy compounds with ($T_{1/2}$, 1 h) values 30-200° C. are effective promoters of the instant hydrosilylation process. Preferably, the concentration of peroxy compound used in the process of the invention ranges from about 1 to about 2000 ppm, more preferably from about 3 to about 1500 ppm, and most preferably from about 5 to about 1000 ppm, all based on the total weight of the reaction mass. Preferred temperature and concentration ranges for the various classes of peroxy compounds are set forth hereinbelow.

Peroxy compounds might be present in some halogenated unsaturated compounds as a result of particular synthetic or manufacturing practices. For example, allyl hydroperoxide ($H_2C=CHCH_2OOH$), 3-chloro,3-hydroperoxy-propene ($H_2C=CHCHClOOH$), and diallyl peroxide ($H_2C=CHCH_2O)_2$ can be generated during the manufacture of allyl chloride as a result of the presence of oxygen during the chlorination of propene. However, these peroxy compounds can be decomposed during purification, storage and transport of the allyl chloride. It will be shown by example that the half-life of peroxy compounds in some allyl chloride samples can be as short as 27 minutes at the normal boiling point (44-45° C.) of allyl chloride. Thus, the half-life will be considerably shorter in the temperature range, 70-100° C., in which the hydrosilylation reactions are performed. Consequently, the concentrations of peroxy compounds will not always be adequate to promote and sustain the hydrosilylation reaction to completion. So variable and inconsistent results are possible in laboratory experiments and commercial operations when the peroxy compounds are not present in effective reaction-promoting concentrations. The present invention discloses the use of peroxy compounds at levels sufficient to sustain effective hydrosilylation. The invention also discloses that analysis of the concentrations of peroxy compounds in unsaturated compounds to be hydrosilylated must reflect what is present just prior to reaction rather than what is present shortly after synthesis or manufacture.

The peroxy compound must be present in the hydrosilylation reaction zone along with the reagents, the ruthenium-containing catalyst and aromatic promoter. It can be injected directly into the reaction zone, or preferably admixed with the olefin. Experiments have shown that the minimally effective and optimally effective use levels vary with the choice of peroxy compound. For example, in the hydrosilylation of allyl chloride with trimethoxysilane, as little as 3 parts per million di-t-butyl peroxide (based on total weight of reaction mass) effect a measurable improvement in the yield of 3-chloropropyltrimethoxysilane. However, maximum yields are observed between 5 and 150 parts per million. Usage in excess of 300 parts per million can result in measurable decreases in product yield. In comparison, 400-750 parts per million t-butyl hydroperoxide afford maximum yield of 3-chloropropyltrimethoxysilane, and with t-butylperoxy-3,5,5-trimethylhexanoate maximum yield remained stable between 350 and 6000 parts per million.

Hydroperoxides, dialkyl peroxides, Group 14 hydroperoxides and peroxides (for example, silyl hydroperoxides and disilyl peroxides), diacyl peroxides, ketone peroxides, peroxy dicarbonates, peroxy esters and peroxy ketals are classes of peroxy compounds, which are effective in the practice of the instant invention. Hydroperoxides, dialkyl peroxides and peroxy esters are preferred.

The hydroperoxides are characterized by the presence of the —O—O—H functional group. In the formulae, R—O—O—H and $R_2C(O-O-H)_2$, R can be linear or branched, saturated or unsaturated, cyclic, aromatic or alkaryl with one to 25 carbon atoms. Examples include t-butyl hydroperoxide, t-amyl hydroperoxide, cumene hydroperoxide, allyl hydroperoxide, tetrahydrofuryl hydroperoxide, limonene hydroperoxides, terpene hydroperoxides, steroidal hydroperoxides and 2,5-dihydroperoxy-2,5-dimethylhexane. Hydroperoxides with ($T_{1/2}$, 1 h) values up to 200° C. are preferred. Allyl hydroperoxide, t-butyl hydroperoxide, tetrahydrofuryl hydroperoxide and cumene hydroperoxide are preferred hydroperoxide promoters for the practice of this invention. Effective levels of allyl hydroperoxide are greater than 10 parts per million. Values in the range 20-100 parts per million are preferred. t-Butyl hydroperoxide and cumene hydroperoxide are effective promoters when used at 50-1000 parts per million. Concentrations of 400-750 parts per million are preferred with t-butyl hydroperoxide and 100-500 with cumene hydroperoxide.

Hydroperoxides in which the —O—O—H group is attached to silicon, germanium and tin are also effective promoters of the inventive hydrosilylation. Group 14 hydroperoxides are represented by Z—O—O—H, in which Z denotes a silyl, germyl or stannyl moiety. Examples are trimethylsilylhydroperoxide, tribenzylsilylhydro-peroxide, tert-butyldimethylsilylhydroperoxide, methyldiphenylsilylhydroperoxide and triphenylsilylhydroperoxide. The chemistry of organosilicon hydroperoxides and peroxides has been reviewed in the literature (see, Y. A. Alexandrov, J. Organometallic Chem., vol. 238 (1982) 1-78, and A. G. Davies, Tetrahedron, vol 63 (2007) 10385-10405), and these references are incorporated by reference herein in their entireties.

Dialkyl peroxides are represented by the general formula, R—O—O—R, in which R has the same meaning as defined hereinabove for the hydroperoxides. Examples are di-t-butyl peroxide, di-t-amyl peroxide, dicumyl peroxide, 2,5-dimethyl-2,5-di(t-butylperoxy)hexane. Dialkyl peroxides with ($T_{1/2}$, 1 h) values 100-160° C. are preferred. Di-t-butyl peroxide and dicumyl peroxide are particularly preferred.

Effective use levels of di-t-butyl peroxide span 3-300 parts per million, preferably 5-150 parts per million and more preferably 5-50 parts per million. With dicumyl peroxide, the effective range is 50-1000 parts per million, preferably 200-400 parts per million.

Diacyl peroxides have the general formula, $(RC(O)O)_2$, in which R is linear or branched, cyclic, aromatic or alkaryl with one to 25 carbon atoms. Examples are didecanoyl peroxide, dilauroyl peroxide and dibenzoyl peroxide. Diacyl peroxides with ($T_{1/2}$, 1 h) values 40-100° C. are preferred. Dibenzoyl peroxide is a preferred peroxide promoter of the instant invention. It is effective when used at 50-2500 parts per million, preferably 150-1000 parts per million relative to the total weight of reactants.

Peroxyesters are represented by the general formula, RC(O)O—OR. R is linear or branched, cyclic, aromatic or alkaryl with one to 25 carbon atoms. However, the R groups in the ester and alcohol fragments of the formula can be different from each other. Examples are cumyl peroxyneodecanoate, t-amyl peroxypivalate and t-butyl peroxy-3,5,5-trimethylhexanoate. The latter is a preferred peroxide promoter of this invention. Preferred peroxyesters possess ($T_{1/2}$, 1 h) values 50-100° C. Concentrations of t-butyl peroxy-3,5,5-trimethylhexanoate greater than about 100 parts per million afford measurable improvements in hydrosilylation rate and yield. Values in the range, 350-6000 parts per million are preferred.

Peroxydicarbonates have the general formula, $(ROC(O)O)_2$, in which R is linear or branched, cyclic, aromatic or alkaryl with one to 25 carbon atoms. Examples are di(n-propyl)peroxydicarbonate and di(2-ethylhexyl)peroxydicarbonate, both of which are preferred promoters of the instant hydrosilylation process. The effective use range of both is 50-3500 parts per million, preferably 100-2000 parts per million. Preferred peroxydicarbonates possess ($T_{1/2}$, 1 h) values 50-75° C.

The general formula, $R_2C(O—O—R')_2$, depicts peroxy ketals. R and R' are linear or branched, cyclic, aromatic or alkaryl with one to 25 carbon atoms. Ethyl-3,3-di(t-butylperoxy)butyrate, 1,1-di(t-butylperoxy)cyclohexane and 1,1-di(t-butyl-peroxy)3,3,5-trimethylcyclohexane are effective examples for the process of this invention. Preferred peroxyketals have ($T_{1/2}$, 1 h) values 100-150° C.

Aromatic Promoters

U.S. Pat. No. 6,872,845, herein incorporated by reference in its entirety, discloses electron-donating aromatic compounds as promoters for ruthenium-catalyzed hydrosilylation of haloolefins by hydridoalkoxysilanes. These additives are optionally used in the process of this invention. Suitable aromatic compounds include, for example, benzene, ethylbenzene, diethylbenzene, triethylbenzene, n-butylbenzene, di-t-butylbenzene, bibenzyl, toluene, t-butyltoluene, anisole, 1-phenylhexane, 1-phenyldodecane, NALKYLENE®. (a mixture of n-alkylbenzenes with alkyl groups of from $C_8$ to $C_{20}$), THERMINOL® (a mixture of diphenylalkanes and bibenzyl isomers), MARLOTHERM® LH (a mixture of benzyl toluenes), MARLOTHERM® S (mixture of dibenzyl toluenes), m-xylene, mesitylene, p-cymene, diphenylmethane, triphenylmethane, phenyl ether, phenothiazine, and biphenyl. They can be present in an amount from about 1 to about 100 mole equivalents per mole of ruthenium metal, preferably from about 5 to about 50 mole equivalents per mole of ruthenium metal and more preferably from about 20 to about 30 mole equivalents per mole of ruthenium metal. Aromatic compounds with normal boiling points above the temperature of the hydrosilylation reaction are preferred.

Ruthenium Catalysts

Suitable ruthenium-metal containing catalysts can be selected from ruthenium metal or homogeneous and heterogeneous ruthenium metal-containing compounds and complexes in which ruthenium can be in any of the oxidation states 0 to 8 inclusive. Examples include the following: Particulate Ru from 1 nanometer to 100 microns; Ru on solid supports such as Ru on Fe, Ru on alumina, Ru on carbon and Ru on silica; ruthenium halides ($RuX_n$, X is halogen atom and n is any value between 2-4), for example $RuCl_3$ and $RuBr_3$; $MRuCl_3$, $M_2Ru_5Cl_{12}$, $M_4Ru_4Cl_{12}$, (M=H, or alkali metal); zinc-reduced and tin-reduced reaction products of ruthenium halides, for example, $ZnRu_5Cl_{12}$ and $SnRu_5Cl_{12}$; $RuO_2$, $Ru_3(CO)_{12}$, $[Ru(CO)_3Cl_2]_2$; cycloolefin complexes of ruthenium such as Ru(COD)(COT), COD-$RuCl_2$, [COD-$RuCl_2]_2$, in which COD is cyclooctadiene and COT is cyclootcatriene; bis(6,6-dimethylcyclopentadienyl)ruthenium, bis($\eta^5$-2,4-dimethylpentadienyl)ruthenium, bis(1,3-dimethylcyclopentadienyl)ruthenium, $Ru(AcAc)_3$ in which AcAc is the acetylacetonate ligand; ($\pi$-arene) ruthenium complexes such as (p-cymene) ruthenium (II) chloride dimer and (benzene) ruthenium (II) chloride dimer; ammine complexes of ruthenium such as $[Ru(NH_3)_6]X_2$ and $[Ru(NH_3)_6]X_3$. In one embodiment, the ruthenium catalyst is substantially free of phosphine, that is, having a phosphine to ruthenium molar ratio of less than $1\times10^{-3}$, and preferably less than $1\times10^{-6}$.

The preferred ruthenium catalysts are the ruthenium chloride compounds, with $RuCl_3$ hydrate and its zinc-reduced product being the most preferred. Catalyst from one batch can be recycled to the next batch without significant loss of activity. Catalyst use level may be in the range of 1 to 300 parts per million of contained Ru metal based on the total reactant charge, with 5 to 50 parts per million being preferred.

Hydrosilylation Process

The hydrosilylation process of the instant invention proceeds advantageously when the ruthenium-containing catalyst solution is sparged with oxygen prior to its injection into the reaction zone. This is accomplished by adding dilute oxygen, as for example, a mixture of 3% $O_2$ in $N_2$, to the catalyst supply and/or the feed stream to the reactor. Additional dilute oxygen in nitrogen, argon, or helium can also be fed into the reaction zone as long as provisions are made to avoid the explosive regimes of the organic compounds in use.

The instant process is advantageously carried out by slowly adding the olefinic halide and a peroxy compound to a reaction medium containing the alkoxysilane and conducting the hydrosilylation in the presence of a oxygen-sparged ruthenium metal-containing catalyst and, optionally, an electron-donating aromatic compound, as an additional promoter, in either a semi-batch or continuous process. This order of addition effectively maintains a minimum concentration of unreacted olefinic halide in the reaction medium relative to the alkoxysilane, and thus effectively establishes a very large molar excess of the alkoxysilane relative to the olefinic halide in the reaction medium. In general practice, the maximum rate of addition of the olefinic halide to the alkoxysilane will be determined by the reaction rate, which is dependent in part on the reaction temperature, the catalyst concentration, the concentration of electron-donating aromatic compound promoter, the concentration and thermal stability of the peroxy compound and by the heat transfer limitations of the reaction equipment, whether a small laboratory reactor or a very large commercial reactor is used, as will be understood by one skilled in the art.

As mentioned above, the process of the invention can be performed in a variety of commercially available equipment arrangements now used for hydrosilylation reactions, including equipment arrangements in which such reactions are performed in continuous fashion. By integrating the present process with a source of trimethoxysilane or triethoxysilane prepared directly from silicon metal and the corresponding alkanol, one can avoid the use of corrosive and hazardous hydridochlorosilanes and eliminate the generation of large amounts of chlorine-containing waste byproducts, which are inherent to the use of products derived from hydridochlorosilanes.

As shown in FIGS. 1, A, B and C are the hydrosilylation reactor, crude product stripping column and catalyst solution supply, respectively. Alkoxysilane (100), olefin (110) and catalyst (130) are inputs to the reactor. The peroxy compound (120) is injected admixed with the olefin (110), but it may also be introduced directly into the reactor (A). The catalyst solution in (C) comprises the ruthenium source, solvent and aromatic hydrocarbon. It is sparged with oxygen diluted in nitrogen (140). Hydrosilylation reaction mixture (160) exits the reactor (A) and enters the stripping column (B), wherein it is separated into stream (150) containing unreacted alkoxysilane, a lower boiling overhead discharge (170) and crude product (180). The alkoxysilane stream (150), which also contains aromatic hydrocarbon and the peroxy compound, is recycled to the reactor (A).

The preferred order of combination can be achieved in semi-batch or continuous operation. In semi-batch operation, a reactor is first charged with a large portion of, and preferably with the full complement of, the molar excess of alkoxysilane. The oxygen-sparged ruthenium catalyst, optionally admixed with the aromatic compound, can then be added to the alkoxysilane. The olefinic halide and the peroxy compound are then introduced simultaneously in separate streams or blended together. As used herein, slow addition of olefinic halide generally means at a rate below about 3 moles of olefinic halide per hour per mole of alkoxysilane, and preferably at or below 1 mole per hour per mole of alkoxysilane. For example, in a semi-batch process, an addition rate of 2 moles of olefinic halide/hour/mole of alkoxysilane is practiced when 1 mole of olefinic halide is added to a reactor containing 2 moles of alkoxysilane in 15 minutes. Once the olefinic halide has been added to the reactor, the reaction is continued until complete conversion of the olefinic halide is obtained. While this, in large part, is a function of temperature, catalyst and aromatic promoter concentration, complete conversion generally can be achieved in 1 to 15 hours and more usually between 1 to 10 hours. Completion of the reaction in 1 to 5 hours is not unusual. Some portion of the alkoxysilane can also be added in admixture with the olefinic halide or simultaneously with the addition of the olefinic halide as a separate stream.

In continuous operation, the reactor typically is charged with separate streams of the olefinic halide (containing the peroxy compound promoter) and alkoxysilane at a mole ratio of alkoxysilane to olefinic halide of from about 1.3 to about 3.0, and preferably at a mole ratio of from about 1.8 to about 2.3. Such operation ensures a proper excess of alkoxysilane in the reaction vessel under steady state operating conditions. For the preferred alkoxysilane, trimethoxysilane, and preferred olefinic halide, allyl chloride, the preferred mole ratio is from about 1.6 to about 2.3. In continuous operation, the aromatic promoter and the ruthenium catalyst can be added to the olefinic halide and alkoxysilane separately, or preferably, as a catalyst solution to the reactor in which the aforementioned separate streams of olefinic halide and alkoxysilane are being charged.

The aromatic promoter employed in the process of this invention must be present in the reaction medium in a reaction-promoting amount, i.e., an amount which is below that which inhibits the reaction (as manifested by higher product purities and/or lowered production of byproducts such as organoalkoxysilanes and haloalkoxysilanes), but which increases the yield of the reaction. In general, an effective amount of aromatic promoter can range from about 1 to about 100 mole equivalents per mole of ruthenium metal and preferably from about 5 to about 50 mole equivalents per mole of ruthenium metal and, more preferably, from about 20 to about 30 mole equivalents per mole of ruthenium metal.

Other hydrosilylation reaction conditions, such as temperature, mole ratios of reactants, pressure, time, and catalyst concentration, are not narrowly critical. One has wide latitude in adjusting these factors to use various pieces of production equipment economically and safely. Such equipment will typically have provisions for heating, cooling, agitation, maintenance of inert atmospheres and purification, as by filtration or distillation. Thus, equipment typically used for large scale commercial hydrosilylation reactions can be used for the process of the present invention, including equipment wherein olefinic halide, containing a peroxy compound promoter, is added to a refluxing, condensable stream of hydridosilicon compound in a zone containing a heterogeneous supported hydrosilation catalyst and an electron-donating aromatic promoter. See, for example, U.S. Pat. Nos. 6,015,920 and 6,872,845, which are both incorporated herein by reference in their entireties.

Reaction conditions can include a reaction temperature of from about 50° C. to about 130° C. with from about 60° C. to 80° C. being preferred. Generally, the process is performed at a pressure at or above atmospheric pressure with atmospheric pressure being preferred. It is recognized that the process of the present invention may provide a high yield of the desired chloroalkylalkoxysilane in a truly batch system. However, a batch reaction will typically be conducted at a lower temperature with consequently longer reaction times. Thus, it is preferred to perform the hydrosilylation at an elevated temperature by adding the peroxy compound enriched olefinic halide to a molar excess of the alkoxysilane in the presence of the ruthenium metal-containing catalyst and an aromatic promoter. One particular preferred mode of operation (semi-batch) involves slowly adding the full complement of peroxy compound enriched olefinic halide over a period of time, to obtain a rate of addition of less than 3 moles of olefinic halide per hour per mole of alkoxysilane, to a reactor containing the full complement of the alkoxysilane, for example, from about 1.6 to about 2.3 molar equivalents of trimethoxysilane relative to the full amount of allyl halide to be added. Preferably, the reactor contains 5 to 50 parts per million of ruthenium as $RuCl_3$ hydrate by weight of total reactants and a reaction-promoting effective amount of aromatic promoter and the reaction is conducted at from about 50° C. to about 130° C. and preferably from about 60° C. to about 80° C. Excess alkoxysilane, ruthenium catalyst and the aromatic promoter can be recycled effectively to the next batch.

Since the process of the present invention is nearly quantitative with respect to the conversion of olefinic halide to the desired haloorganoalkoxysilane product, particularly in the reaction of allyl chloride with trimethoxysilane to provide chloropropyltrimethoxysilane, the generation of undesired byproducts is greatly lowered. This reduces the amounts of materials to be destroyed or discarded as waste, to be isolated as separate streams, as by distillation, or to be vented from the reaction system. Since the process of the present invention is highly exothermic, sustained external heating is not normally necessary and reaction times are correspondingly shorter. Generally, the only impurities in significant amounts that need to be removed from the reaction product are the small excess of unreacted alkoxysilane, tetraalkoxysilane, residual catalyst and aromatic promoter. These may be recycled to the next batch without purification. The low level of residual halide that may be present in the product can be neutralized by methods well known in the art. Where the hydrosilylation product of the present invention is used as an intermediate for the production of other organofunctional silicon compounds, its purity on initial synthesis may be sufficient that further purification, such as by distillation, may not be needed.

When applied, e.g., to the preparation of chloropropyltrimethoxysilane, the process of the present invention provides a higher yield of this product, calculated on a molar basis from the limiting reactant, than any one-step or two-step process described in the prior art. This is accomplished through the addition of an effective amount of a peroxy compound promoter in combination with effective levels of an aromatic promoter and a ruthenium catalyst. The process also obtains such yields using significantly lower levels of ruthenium metal-containing catalyst than any process described in the art. The process also provides a higher yield per unit volume of equipment used, since use of inert solvents is obviated and significant quantities of waste byproducts are not generated.

While the process of the present invention does not require operation at a pressure above atmospheric pressure, an elevated pressure may be used, for example up to two atmospheres pressure, to control inadvertent potential emissions of allyl halide to the environment by using a closed reactor. A pressure below atmospheric pressure may be used if a reaction temperature below the atmospheric pressure boiling point of the alkoxysilane is desired.

The haloorganoalkoxysilane product of the process of the present invention may be purified by standard means, as by distillation, or where used as intermediates for a subsequent preparation, may be used directly without intermediate purification.

Whereas the exact scope of the present invention is set forth in the appended claims, the following specific examples illustrate certain aspects of the present invention and, more particularly, point out the various aspects of the method for evaluating the same. However, the examples are set forth for illustrative purposes only and are not to be construed as limitations on the present invention.

EXAMPLES

The following abbreviations and trade names (with their descriptions) appear in the examples:

TABLE 1

Abbreviations

| ABBREVIATION | MEANING | ABBREVIATION | MEANING |
|---|---|---|---|
| g | gram | GC | Gas Chromatography |
| ppm | parts per million | MS | Mass Spectrometry |
| wt % | weight percent | NMR | Nuclear Magnetic Resonance |
| kg | kilogram | ESR | Electron Spin Resonance |
| h | hour | FTIR | Fourier Transform Infra Red |
| min | minute | HPLC | High Pressure Liquid Chromatography |
| s | second | TMS | $HSi(OCH_3)_3$ |
| TMOS | $Si(OCH_3)_4$ | Cl-TMS | $ClSi(OCH_3)_3$ |
| Propyl-TMS | n-$C_3H_7Si(OCH_3)_3$ | Cl-CPCDMS | $ClCH_2CH_2CH_2Si(OCH_3)_2Cl$ |
| mmole | millimole | CPTMS | $ClCH_2CH_2CH_2Si(OCH_3)_3$ |
| | | Bis(TMS)propane | $(H_3CO)_3SiCH_2CH_2CH_2Si(OCH_3)_3$ |

TABLE 2

Hydroperoxides And Peroxides Used In The Illustrated Examples

| ABBREVIATION | MEANING |
|---|---|
| DTBP | $t-C_4H_9-O-O-t-C_4H_9$ |
| TBHP | $t-C_4H_9-O-O-H$ |
| DICUP | $C_6H_5(CH_3)_2C-O-O-C(CH_3)_2C_6H_5$ |
| CUHP | $C_6H_5(CH_3)_2C-O-O-H$ |
| TBCUP | $C_6H_5(CH_3)_2C-O-O-t-C_4H_9$ |
| ALHP | $H_2C=CHCH_2OOH$ |
| DALP | $H_2C=CHCH_2OOCH_2CH=CH_2$ |
| TRIGONOX ® 42S | $t-C_4H_9-O-O-C(O)-CH_2CH(CH_3)CH_2C(CH_3)_3$ |

Trimethoxysilane for the illustrative examples was produced by the Direct Reaction of methanol and silicon as disclosed in U.S. Pat. Nos. 4,727,173, 5,728,858, 5,783,720 and related patents.

Commercial ruthenium trichloride hydrate was the source of ruthenium unless otherwise stated. Elemental analysis gave 33.88 wt % Cl and 38.33 wt % Ru, which corresponds to the mixed Ru(II)/Ru(III) composition, $RuCl_2.RuCl_3 0.3H_2O$. This salt was used either as a 15 wt % solution in methanol (RUCAT1) or as a 7.5 wt % in methanol (67 wt %), which also contained 25.5 wt % diphenylmethane. The latter will be referred to as RUCAT 2. Ruthenium concentration was 48.70 g per liter in RUCAT 1 and 22.51 g per liter in RUCAT 2.

Both RUCAT 1 and RUCAT 2 were characterized by electron spin resonance (ESR) spectroscopy using a Bruker ER 200 instrument. At 77 K, both displayed g tensors at 2.72 and 2.52, relative to DPPH (diphenylpicrylhydrazyl) at g 2.0035. Freshly prepared RUCAT 1 showed very low ESR intensity. Intensity increased to maximum values after 12-18 hours. No spectral differences were observed before and after extensive freeze-thaw degas cycles of both RUCAT 1 and RUCAT 2.

All allyl chloride samples used in the experiments were standard reagent grade materials obtained from commercial suppliers. They were stored in closed metal containers or in opaque glass containers within closed metal cans when not in use. Table 3 sets forth the concentration ranges of allyl chloride and the principal impurities.

TABLE 3

Composition Of Allyl Chloride Used In Examples

| COMPONENT | RANGE, wt % | COMPONENT | RANGE, wt % |
|---|---|---|---|
| Allyl Chloride | 98.75-99.35 | 1-Chloro-2-methyl-propane | 0.01-0.05 |
| 2-Chloropropene | 0.004-0.02 | Cyclohexane | 0.04-0.15 |
| 2-Chloropropane | 0.20-0.51 | Cyclohexene | 0.002-0.014 |
| 1-Chloro-1-propene (cis/trans) | 0.03-0.07 | Benzene | 0.001-0.01 |
| 1-Chloropropane | 0.19-0.24 | 3,3-Dichloropropene | 0.001-0.02 |
| 4-Methyl-1-pentene | 0.006-0.01 | Water, ppm | 9-25 |
| 1,5-Hexadiene | 0.08-0.21 | HCl, ppm | 6-15 |
| 2,2-Dichloropropane | 0.003-0.023 | Propylene oxide Epichlorohydrin | |
| Cyclopentyl compounds | | | |

Peroxide Analyses

Analysis of allyl chloride for hydroperoxide and peroxide content was typically done just prior to use of the material in hydrosilylation experiments. Iodometric titration, HPLC and visually indicating test strips were used. Iodometric titration is suitable for the determination of easily reduced peroxy compounds such as hydroperoxides and diacyl peroxides (see R. D. Mair and R. T. Hall in Organic Peroxides, D. Swern (Editor), pp 579-599, chp. 4, John Wiley & Sons, NY, 1971). QUANTOFIX™ and EM QUANT™ peroxide test strips covering concentration ranges up to 1000 ppm afforded rapid determination of hydroperoxide concentrations. Whereas sodium borohydride reacts only with hydroperoxides, triphenylphosphine reacts with all classes of peroxy compounds. This difference enabled distinguishing the effects of the various peroxy compounds. The reaction of triphenylphosphine with peroxy compounds was used (see A. W. P. Jarvie, et al., J. Polymer Science: Part A-1 vol 9 (1971) pp 3105-3114) as the basis of an HPLC method for determination of total peroxide. The cited publication by Jarvie, et al. is fully incorporated herein by reference. Gas chromatography was used to analyze for specific peroxy compounds (for example, di-t-butyl peroxide) in the chloropropyltrimethoxysilane reaction product.

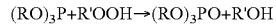
$(RO)_3P + R'OOH \rightarrow (RO)_3PO + R'OH$

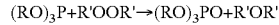
$(RO)_3P + R'OOR' \rightarrow (RO)_3PO + R'OR'$

Laboratory Reaction

The laboratory reactor was a 4-necked, 100 ml round bottom flask supported in a temperature-controlled heating mantle on a magnetic stirrer. A reflux condenser cooled to −25° C. was attached to the central opening of the flask. The refrigerant was 10 centistokes silicone oil. A syringe pump for allyl chloride injection, a thermocouple and an infrared monitoring probe were attached to the three peripheral flask openings. The thermocouple was attached to a computer-controlled heating unit. Visual display of the temperature profile afforded clear indication of the reaction exotherm and its duration. Infrared spectroscopy was used to monitor the disappearance of the SiH functionality. Both air and nitrogen were available for sweeping the outlet of the reflux condenser.

A thorough nitrogen purge of the assembled, dried glassware was done at ambient temperature prior to the start of each experiment. Trimethoxysilane (typically 34-36 g) was added to the flask along with selected microliter volumes of a ruthenium-containing catalyst solution of known ruthenium concentration. The aromatic promoter was usually present in the ruthenium catalyst solution. However, some experiments were conducted without it. The contents of the flask were stirred and heated to 75° C. and the baseline infrared spectra were recorded. Meanwhile, allyl chloride (12-14 g), with or without added peroxy compound, was charged to the syringe, which was then affixed to the pump. Occasionally, the peroxy compound was added directly to the trimethoxysilane-ruthenium catalyst mixture in the flask. Color, temperature and infrared spectroscopic changes were monitored during and after the addition of allyl chloride. Reaction mixtures were analyzed by gc, gc/ms and $^1H$, $^{13}C$, $^{29}Si$ NMR.

Allyl chloride addition (0.21 g/min) was initiated with the flask contents at 75° C. An increase in the temperature was observed after the addition of a few drops of allyl chloride. The exotherm rose to 85-100° C. within a few minutes depending on the reactivity of the allyl chloride and the ruthenium concentration. Temperature remained relatively stable at the higher value while allyl chloride was still being fed. It decreased sharply following the termination of allyl chloride injection.

Examples 1-15

Examples 1-15 illustrate the inconsistent performance of standard, commercial grade allyl chloride in the ruthenium-catalyzed hydrosilylation reaction with trimethoxysilane. All reactions were performed in the laboratory glassware described above with 32.5 µL RUCAT 2 as the catalyst source. The ruthenium concentration was 20.9 ppm based on the weight of TMS charged.

Table 4 shows data for the allyl chloride content of the reaction mixtures. Residual allyl chloride greater than 0.2 wt % indicates incomplete reaction. Clearly, hydrosilylation was not complete in 6 of the 15 samples tested. These experiments (Examples 1, 2, 6, 13, 14, 15) showed exotherms that were less than 6° C. with CPTMS less than 68 wt % in the reaction mixtures. The experiments in which there was no gc detectable allyl chloride all showed exotherms that were larger than 8° C. and had CPTMS greater than 70 wt % in the reaction mixtures.

TABLE 4

Residual Allyl Chloride In Reaction Mixtures From The Experiments Of Examples 1-15

| EXAMPLE AND SAMPLE | RESIDUAL ALLYL CHLORIDE, wt % |
|---|---|
| EX 1. D1834 | 0.3 |
| EX 2. D3721 | 21 |
| EX 3. D1941 | 0 |
| EX 4. D6009 | 0 |
| EX 5. D5644 | 0 |
| EX 6. DTT1 | 20 |
| EX 7. DCAR3 | 0 |
| EX 8. DSPLK1 | 0 |
| EX 9. DSPLK2 | 0 |
| EX 10. DSPLK3 | 0 |
| EX 11. DALD1 | 0 |
| EX 12. DSOLV1 | 0 |
| EX 13. DLEND1 | 20 |
| EX 14. DLEND2 | 23 |
| EX 15. DLEND3 | 16 |

Inconsistent reactivity was also observed in a commercial hydrosilylation process, wherein 21 of 40 allyl chloride lots showed poor reactivity.

Examples 16-18

Examples 16-18 illustrate that neither the concentration of ruthenium nor the presence of diphenylmethane was a contributing factor in the incomplete hydrosilylation observed in Example 6.

The experiments of Examples 6, 7 and 10 were repeated with RUCAT 1 as the catalyst. They are Examples 16, 17 and 18, respectively. In all three, the ruthenium concentration was 45.2 ppm based on the weight of TMS charged. No exotherm was observed in Example 16 and the residual allyl chloride was 32.6 wt %. A 9° C. exotherm was observed in Example 17 and a 7.4° C. one in Example 18. There was no GC detectable allyl chloride in either of these reaction mixtures.

Examples 19-20

Examples 19 and 20 illustrate the hydrosilylation reactivity of allyl chloride is improved when the samples are exposed to ambient room light and/or ultraviolet light. Allyl chloride (D3721) used in Example 2 was used in Examples 19A-D. Examples 20A-C were run with the allyl chloride (DTT1), which was used in Example 6. Portions of these allyl chloride samples were set aside in the dark or were exposed to light for the periods of time set forth in Table 5. Hydrosilylation reactions were later done with trimethoxysilane and RUCAT 2 according to standard procedure described hereinabove. The reactions of Examples 19A-D were done with 15 g TMS, 5.56 g allyl chloride and 17 μL RUCAT 2. Those of Examples 20A-C used 35 g TMS, 14 g allyl chloride and 32 μL RUCAT 2. Ru concentration was 25.5 ppm in Examples 19A-D and 20.6 ppm in Examples 20A-C. Reaction results are summarized in Table 5. CPTMS and allyl chloride values reported are for the reaction products free of excess TMS.

TABLE 5

DATA FOR EXAMPLES 19A-19D AND 20A-20C

| Example | Allyl Chloride Sample | Exotherm, ° C. | Residual Allyl Chloride, wt % | CPTMS, wt % |
|---|---|---|---|---|
| 19A | D3721 as received | 3.9 | 21 | 66 |
| 19B | Stored 2 weeks in dark in clear bottle | 4.1 | 12 | 79 |
| 19C | Ambient room light 3 days in clear bottle | 8.9 | 0.03 | 90 |
| 19D | Exposed to UV light 60 h | 9.1 | 0.03 | 92 |
| 20A | DTT1 as received | 2.8 | 5.3 | 85.5 |
| 20B | UV light 2 weeks in clear bottle | 8.8 | 0 | 91.9 |
| 20C | UV light 14 weeks in clear bottle | 9.6 | 0 | 94.3 |

The results of Examples 19C and 19D, when compared with those of Examples 19A and 19B, show that allyl chloride reactivity improved and the yield of CPTMS increased when the samples were exposed to light. The same conclusion applies to the results of Examples 20 B and 20C in relation to Example 20A. Both sets of results suggest that peroxy compounds, which were lacking in the 'as received' samples of allyl chloride, but were generated by exposure of these samples to ultraviolet light, exert a positive influence on the hydrosilylation of allyl chloride by TMS.

Examples 21A-21C

Examples 21A-21C illustrate that peroxy compounds exert a positive influence on the hydrosilylation of allyl chloride by trimethoxysilane. The hydrosilylation reactions of Example 21A and 21C were done in a nitrogen atmosphere and that of Example 21B in air. An addition of 120 microliters of tetrahydrofuran (THF), which was believed to contain tetrahydrofuryl hydroperoxide, was made to the allyl chloride used in Example 21C. All three experiments were run with allyl chloride from the same container and lot. Experimental details and analyses of the reaction mixtures are summarized in Table 6.

As shown in Examples 21A, 21B, and 21C, replacement of the nitrogen atmosphere with air caused more consumption of both reagents (allyl chloride and trimethoxy-silane) and increased formation of chloropropyltrimethoxysilane (CPTMS). Improvement was also marked in Example 21C, wherein the nitrogen atmosphere of Example 21A was maintained, but a very small amount of hydroperoxide-containing tetrahydrofuran was added to the allyl chloride.

TABLE 6

Effect of Air and Tetrahydrofuranyl Hydroperoxide on Allyl Chloride Hydrosilylation

|  | EXAMPLE 21A | EXAMPLE 21B | EXAMPLE 21C |
|---|---|---|---|
| Allyl Chloride, g | 13.4 | 13.4 | 13.4 |
| Trimethoxysilane, g | 34.2 | 34.2 | 34.2 |
| RUCAT2, μL | 32.5 | 32.5 | 32.5 |
| Ru, ppm | 21.4 | 21.4 | 21.4 |
| Atmosphere | $N_2$ | Air | $N_2$ |
| Additive | None | None | 120 μL, THF |
| Exotherm ° C. | None | 2.3 | 2.9 |
| Residual Allyl Chloride, wt % | 15.20 | 3.80 | 5.10 |
| TMS, wt % | 44.46 | 30.07 | 33.46 |
| TMOS, wt % | 4.23 | 4.88 | 4.03 |
| CPTMS, wt % | 35.81 | 61.25 | 57.41 |

Examples 22A-22M

These Examples show that hydroperoxides and other peroxy compounds are present in allyl chloride and that acceptable hydrosilylation can still occur if the hydroperoxides are selectively destroyed. As background, recall that ascorbic acid, ascorbates and sodium borohydride destroy (react with) only hydroperoxides and not the peroxides, while organophosphites destroy hydroperoxides and peroxides. The iodine test (sodium iodide plus acetic acid) detects all hydroperoxides, but peroxide detection depends on the ease of reducibility of the peroxide. Normal alkyl peroxides are more readily reducible than tertiary alkyl and aromatic peroxides. (See R. D. Mair and R. T. Hall, *Determination of Organic Peroxides in Treatise on Analytical Chemistry, Volume* 14, *Part II*, Wiley—Interscience, NY, 1971. pp 385-388)

Two allyl chloride lots, both of which had demonstrated acceptable hydrosilylation activity and selectivity with trimethoxysilane to produce 3-chloropropyltrimethoxysilane (CPTMS), were used in the experiments of these Examples. Samples of both allyl chloride lots were first analyzed by iodometry for total peroxides and with the QUANTOFIX® or EM QUANT® test strips for hydroperoxides. Next, about 100-200 g of each was treated with sodium borohydride (EXAMPLES 22A, 22B and 22D), or ascorbic acid (EXAMPLE 22C) or diisodecylphenyl-phosphite (EXAMPLES 22E-22G) or tributylphosphite (EXAMPLE 22H-22L), or dimethyl phosphite (EXAMPLE 22M) and kept in the dark overnight or for a number of days, as outlined in the Tables below. Tests with the QUANTOFIX® or EM QUANT® test strips for hydroperoxides, or with acetic acid plus sodium iodide for total peroxides, were repeated before the hydrosilylation reactions with trimethoxysilane. Hydrosilylations were done with 12-14 g allyl chloride (AC) and 34-36 g trimethoxysilane (TMS) and either 32 μL RUCAT2 or 15 μL RUCAT1, as described in the general procedure above. Results are summarized in the following Tables.

TABLE 7

Example 22A Data

| STEP | ACTION | RESULT | | | | |
|---|---|---|---|---|---|---|
| 1 | Test with QUANTOFIX ® strips | 150-300 ppm hydroperoxide | | | | |
| 2 | Analyze by iodometry | 808 ± 25 ppm total peroxide | | | | |
| 3 | Hydrosilylation of 12.6 g AC with 34.2 trimethoxysilane and RUCAT2 | ΔT ° C. 7 | AC % 0.02 | TMS % 22.4 | TMOS % 4.28 | CPTMS % 73.30 |
| 4 | Stir 100 g AC with 0.5 g NaBH$_4$ overnight in dark bottle | Hydroperoxides destroyed | | | | |
| 5 | Test AC with QUANTOFIX ® strips | 0-1 ppm hydroperoxide | | | | |
| 6 | Hydrosilylation of 12.58 g with 34.0 trimethoxysilane and RUCAT2 | ΔT ° C. 19.9 | AC % 0.12 | TMS % 15.89 | TMOS % 4.56 | CPTMS % 79.43 |

The difference in the analytical results obtained with the QUANTOFIX® test strips and the iodometric titrations suggested that peroxy compounds other than hydroperoxides were present in the two allyl chloride lots. Hydroperoxide concentration was 0-1 ppm in Examples 22A and 22B after the NaBH$_4$ treatment and was 1-3 ppm after ascorbic treatment in Example 23C. After treatment with NaBH$_4$ (Examples 22A and 22B) or ascorbic acid (Example 22C) to destroy hydroperoxides, both lots still showed acceptable hydrosilylation performance.

TABLE 8

Example 22B Data

| STEP | ACTION | RESULT | | | | |
|---|---|---|---|---|---|---|
| 1 | Test with QUANTOFIX ® strips | 50-150 ppm hydroperoxide | | | | |
| 2 | Analyze by iodometry | 665 ± 50 ppm total peroxide | | | | |
| 3 | Hydrosilylation of 12.6 g with 34.2 g trimethoxysilane and RUCAT2 | ΔT ° C. 12.7 | AC % 0.07 | TMS % 19.70 | TMOS % 4.17 | CPTMS % 76.06 |
| 4 | Stir 100 g with 0.5 g NaBH$_4$ overnight in dark bottle | — | | | | |
| 5 | Test with QUANTOFIX ® strips | 0-1 ppm hydroperoxide | | | | |
| 6 | Hydrosilylation of 12.6 g AC with 34.2 g trimethoxysilane and RUCAT2 | ΔT ° C. 11.4 | AC % 0.04 | TMS % 19.15 | TMOS % 3.72 | CPTMS % 77.09 |

TABLE 9

Example 22C Data

| STEP | ACTION | RESULT |
|---|---|---|
| 1 | Test with QUANTOFIX ® strips | 50-150 ppm hydroperoxide |
| 2 | Analyze by iodometry | 665 ± 50 ppm total peroxide |

TABLE 9-continued

Example 22C Data

| STEP | ACTION | RESULT | | | | |
|---|---|---|---|---|---|---|
| 3 | Hydrosilylation of 12.6 g AC with 34.2 g trimethoxysilane and RUCAT2 | ΔT ° C. 12.7 | AC % 0.07 | TMS % 19.70 | TMOS % 4.17 | CPTMS % 76.06 |
| 4 | Stir 100 g AC with 2.5 g Ascorbic Acid 7 days at RT in dark bottle | | | | | |
| 5 | Test with QUANTOFIX ® strips | 1-3 ppm hydroperoxide | | | | |
| 6 | Hydrosilylation of 12.6 g AC with 34.4 g trimethoxysilane and RUCAT2 | ΔT ° C. 15.5 | AC % 0.03 | TMS % 18.92 | TMOS % 4.33 | CPTMS % 76.72 |

Allowing for the presence of excess TMS in the reaction mixtures, CPTMS yield was 94.46% in the control reaction (Step 3) of Example 22A and 94.44% in the NaBH$_4$ treated sample (Step 6). Similarly, CPTMS yield was 94.72% in the control reaction (Step 3) of Examples 22B and 22C and 95.35% and 94.62% in the treated NaBH$_4$ and ascorbic acid samples, respectively. The positive iodometric test in Step 6 of Example 22D also confirms the presence of peroxides in the allyl chloride after the hydroperoxides had been destroyed by NaBH$_4$. The peroxy compounds promoted the hydrosilylation reactions.

TABLE 10

Example 22D Data

| STEP | ACTION | RESULT | | | | |
|---|---|---|---|---|---|---|
| 1 | Test with QUANTOFIX ® strips | 50-150 ppm hydroperoxide | | | | |
| 2 | Analyze by iodometry | 665 ± 50 ppm total peroxide | | | | |
| 3 | Hydrosilylation of 12.6 g AC with 34.2 g trimethoxysilane and RUCAT2 | ΔT ° C. 12.7 | AC % 0.07 | TMS % 19.70 | TMOS % 4.17 | CPTMS % 76.06 |
| 4 | Treat 100 g with 0.5 g NaBH$_4$ overnight in dark bottle | | | | | |
| 5 | Test with QUANTOFIX ® strips | 0-1 ppm hydroperoxide | | | | |
| 6 | Test with CH$_3$COOH and NaI, 48 h | Colorless at 4 h, violet at 48 h due to iodine formation. | | | | |

TABLE 11

Example 22E Data

| STEP | ACTION | RESULT | | | | |
|---|---|---|---|---|---|---|
| 1 | Test with QUANTOFIX ® strips | 50-150 ppm hydroperoxide | | | | |
| 2 | Analyze by iodometry | 665 ± 50 ppm total peroxide | | | | |
| 3 | Hydrosilylation of 12.6 g AC with 34.2 g trimethoxysilane and RUCAT2 | ΔT ° C. 12.7 | AC % 0.07 | TMS % 19.70 | TMOS % 4.17 | CPTMS % 76.06 |
| 4 | Treat 101.6 g AC with 0.051 g DDPP overnight in dark bottle | ~500 ppm DDPP | | | | |
| 5 | Test with QUANTOFIX ® strips | 25-30 ppm hydroperoxide | | | | |
| 6 | Hydrosilylation of 12.6 g AC with 34.2 g trimethoxysilane and RUCAT2 | ΔT ° C. 17.7 | AC % 0.06 | TMS % 20.21 | TMOS % 5.07 | CPTMS % 74.65 |

TABLE 12

Example 22F Data

| STEP | ACTION | RESULT |
|---|---|---|
| 1 | Test with QUANTOFIX ® strips | 50-150 ppm hydroperoxide |
| 2 | Analyze by iodometry | 665 ± 50 ppm total peroxide |

TABLE 12-continued

Example 22F Data

| STEP | ACTION | RESULT |
|---|---|---|
| 3 | Hydrosilylation of ~13 g with trimethoxysilane and RUCAT2 | ΔT ° C.   AC %   TMS %   TMOS %   CPTMS %<br>12.7      0.07    19.70    4.17       76.06 |
| 4 | Stir 102.6 g with 0.103 g DDPP overnight in dark bottle | ~1000 ppm DDPP |
| 5 | Test with QUANTOFIX ® strips | 3-5 ppm hydroperoxide |
| 6 | Hydrosilylation of 12 6 g AC with 34.1 g trimethoxysilane and RUCAT2 | ΔT ° C.   AC %    TMS %   TMOS %   CPTMS %<br>4.5       23.04   58.44    4.31       14.22 |

TABLE 13

Example 22G Data

| STEP | ACTION | RESULT |
|---|---|---|
| 1 | Test with QUANTOFIX ® strips | 50-150 ppm hydroperoxide |
| 2 | Analyze by iodometry | 665 ± 50 ppm total peroxide |
| 3 | Hydrosilylation of 12.6 g AC with 34.2 g trimethoxysilane and RUCAT2 | ΔT ° C.   AC %   TMS %   TMOS %   CPTMS %<br>12.7      0.07    19.70    4.17       76.06 |
| 4 | Treat 102.1 g AC with 0.255 g DDPP overnight in dark bottle | ~2500 ppm DDPP |
| 5 | Test with QUANTOFIX ® strips | 1-3 ppm hydroperoxide |
| 6 | Hydrosilylation of 12.7 g AC with 34.2 g trimethoxysilane and RUCAT2 | ΔT ° C.   AC %    TMS %   TMOS %   CPTMS %<br>0.3       26.56   68.10    3.83       1.52 |

TABLE 14

Example 22H Data

| STEP | ACTION | RESULT |
|---|---|---|
| 1 | Test with QUANTOFIX ® strips | 50-150 ppm hydroperoxide |
| 2 | Analyze by iodometry | 665 ± 50 ppm total peroxide |
| 3 | Hydrosilylation of 13.1 g AC with 35.5 g trimethoxysilane and RUCAT2 | ΔT ° C.   AC %   TMS %   TMOS %   CPTMS %<br>16.8      0.09    23.70    5.07       71.14 |
| 4 | Treat 100 g AC with 0.05 g TBP overnight in dark bottle | 500 ppm TBP |
| 5 | Analyze with iodometry | 225 ± 4 ppm peroxide |
| 6 | Hydrosilylation of 13.1 g AC with 35.6 g trimethoxysilane and RUCAT2 | ΔT ° C.   AC %   TMS %   TMOS %   CPTMS %<br>16.2      0.08    24.11    4.64       71.18 |

TABLE 15

Example 22J Data

| STEP | ACTION | RESULT |
|---|---|---|
| 1 | Test with QUANTOFIX ® strips | 50-150 ppm hydroperoxide |
| 2 | Analyze by iodometry | 665 ± 50 ppm total peroxide |
| 3 | Hydrosilylation of 13.1 g AC with 35.5 g trimethoxysilane and RUCAT1 | |
| 4 | Treat 100 g AC with 0.05 g TBP overnight in dark bottle | 500 ppm TBP |
| 5 | Analyze with iodometry | 225 ± 4 ppm peroxide |
| 6 | Hydrosilylation of 13.0 g with 35.3 g trimethoxysilane and RUCAT1 | ΔT ° C.   AC %   TMS %   TMOS %   CPTMS %<br>14         0.09    21.71    5.55       72.64 |

TABLE 16

Example 22K Data

| STEP | ACTION | RESULT | | | | |
|---|---|---|---|---|---|---|
| 1 | Test with QUANTOFIX ® strips | 50-150 ppm hydroperoxide | | | | |
| 2 | Analyze by iodometry | 665 ± 50 ppm total peroxide | | | | |
| 3 | Hydrosilylation of 13.1 g AC with 35.5 g trimethoxysilane and RUCAT2 | ΔT ° C.<br>16.8 | AC %<br>0.09 | TMS %<br>23.70 | TMOS %<br>5.07 | CPTMS %<br>71.14 |
| 4 | Treat 100 g AC with 0.1 g TBP overnight in dark bottle | 1000 ppm TBP | | | | |
| 5 | Analyze with iodometry | 162 ± 19 ppm peroxide | | | | |
| 6 | Hydrosilylation of ~13 g with trimethoxysilane and RUCAT2 | ΔT ° C.<br>4.6 | AC %<br>21.79 | TMS %<br>57.10 | TMOS %<br>4.86 | CPTMS %<br>16.25 |

TABLE 17

Example 22L Data

| STEP | ACTION | RESULT | | | | |
|---|---|---|---|---|---|---|
| 1 | Test with QUANTOFIX ® strips | 50-150 ppm hydroperoxide | | | | |
| 2 | Analyze by iodometry | 665 ± 50 ppm total peroxide | | | | |
| 3 | Hydrosilylation of 13.1 g AC with 35.5 g trimethoxysilane and RUCAT2 | ΔT ° C.<br>16.8 | AC %<br>0.09 | TMS %<br>23.70 | TMOS %<br>5.07 | CPTMS %<br>71.14 |
| 4 | Treat 100 g AC with 0.25 g TBP overnight in dark bottle | 2500 ppm TBP | | | | |
| 5 | Analyze with iodometry | 8 ± 2 ppm peroxide | | | | |
| 6 | Hydrosilylation of 13.1 g AC with 35.4 g trimethoxysilane and RUCAT2 | ΔT ° C.<br>1.6 | AC %<br>24.98 | TMS %<br>65.00 | TMOS %<br>5.00 | CPTMS %<br>5.02 |

TABLE 18

Example 22M Data

| STEP | ACTION | RESULT | | | | |
|---|---|---|---|---|---|---|
| 1 | Test with EM QUANT ™ strips | 100-1000 ppm hydroperoxide | | | | |
| 2 | Analyze by iodometry | 665 ± 50 ppm total peroxide | | | | |
| 3 | Hydrosilylation of 12.6 g AC with 34.2 g trimethoxysilane and RUCAT2 | ΔT ° C.<br>12.7 | AC %<br>0.07 | TMS %<br>19.70 | TMOS %<br>4.17 | CPTMS %<br>76.06 |
| 4 | Treat 100 g AC with 0.04 g DMP overnight in dark bottle | 400 ppm DMP | | | | |
| 5 | Test with EM QUANT ™ strips | 0.5-25 ppm hydroperoxide | | | | |
| 6 | Hydrosilylation of 12.8 g A withC 34.5 g trimethoxysilane and RUCAT2 | ΔT ° C.<br>4.6 | AC %<br>21.68 | TMS %<br>66.64 | TMOS %<br>4.37 | CPTMS %<br>7.31 |

In Examples 22E-22G, CPTMS formation decreased with increasing DDPP addition to allyl chloride. Analysis of the data for the control reaction (Step 3 in Tables 22E-22G) and the reactions of the DDPP-treated samples (Step 6 in Tables 22E-22G) shows that CPTMS yield declined from 94.72% in the control to 93.55% when DDPP concentration was 500 ppm in allyl chloride. Yield decreased further to 34.22% and 4.76% as DDPP was increased to 1000 ppm and 2500 ppm, respectively. The reduced CPTMS formation observed in Examples 22E-22G and the acceptable performance in Examples 22H and 22J confirm that peroxide functionality in allyl chloride was drastically reduced by 0.0723 mmole DDPP (Example 22G), by 0.053 mmole TBP (Example 22K) and by 0.0465 mmole DMP (Example 22M), but not by 0.0262 mmole TBP (Examples 22H and 22J) or 0.0144 mmole DDPP (Example 22E). Phosphates are formed when peroxy compounds oxidize phosphites. Control experiments have established that up to 0.7 mmole trimethylphosphate in 35 g TMS did not inhibit allyl chloride hydrosilylation.

When the phosphite is present in the TMS-ruthenium catalyst mixture and the allyl choride pumped into it, a stoichiometric excess of phosphite can exist relative to peroxy functionality in the allyl chloride. Consequently, inhibition of the hydrosilylation is quite pronounced. Inhibition was observed in this mode with as little as ~$1 \times 10^{-5}$ millimole $(CH_3O)_2POH$ in 35 g TMS.

Example 23A-23B

Examples 23A-23B illustrate the determination of the half-life of the peroxy compounds present in allyl chloride. It also shows that the half-life is not necessarily the same in different lots of allyl chloride. The allyl chloride lots chosen for the experiments had earlier shown excellent reactivity and selectivity to CPTMS in the hydrosilylation reaction with trimethoxysilane. At the outset, an initial sample (~5 g) of each allyl chloride lot was placed in a dark bottle and stored in ice for later treatment with triphenyl phosphite and analysis of the triphenyl phosphate formed by HPLC as described above.

Each experiment was conducted in a three-necked round bottom flask fitted with a reflux condenser with distillation head, thermocouple and magnetic stir bar. A serum cap was affixed to the third opening of the flask. A second thermocouple was placed at the top of the reflux condenser at the exit point of the distillation head. After the flask had been flushed with nitrogen, 110 g allyl chloride was introduced and all three necks were closed. Heating then commenced. Reflux (44.4° C.) was achieved in 20 minutes. Samples (~5 g) were withdrawn by syringe, through the serum cap, into dark bottles at 30-minute intervals from the start of heating. They were stored in ice for subsequent analysis. Analysis was performed immediately afterwards on the same day. Tables 19 and 20 summarize the experimental results.

TABLE 19

Data For Example 23A

| SAMPLE | TIME, h | Triphenyl Phosphate, ppm | PEROXIDE, ppm | Ln (PEROXIDE) |
|---|---|---|---|---|
| 1 | 0 | 6972.89 | 677.62 | 6.519 |
| 2 | 0.5 | 2314.39 | 224.90 | 5.416 |
| 3 | 1.0 | 1259.16 | 122.36 | 4.807 |
| 4 | 1.5 | 525.24 | 51.04 | 3.933 |
| 5 | 2.5 | 137.26 | 13.34 | 2.591 |

A plot of Ln(Peroxide) versus time yielded a straight line with correlation coefficient $R^2=0.9915$, and equation, Ln(Peroxide)=−1.5407t+6.3477. The half-life=(Ln(2)/1.5407)=0.449 h=26.99 minutes.

TABLE 20

Data For Example 23B

| SAMPLE | TIME, min | Triphenyl Phosphate, ppm | PEROXIDE, ppm | Ln (PEROXIDE) |
|---|---|---|---|---|
| 1 | 0 | 1386.95 | 136.02 | 4.913 |
| 2 | 20 | 1322.52 | 129.70 | 4.865 |
| 3 | 30 | 1294.29 | 126.93 | 4.844 |
| 4 | 30 | 1296.24 | 127.13 | 4.845 |
| 5 | 60 | 1247.61 | 122.36 | 4.807 |
| 6 | 90 | 1227.60 | 120.39 | 4.791 |
| 7 | 120 | 1169.46 | 114.69 | 4.742 |
| 8 | 180 | 1081.05 | 106.02 | 4.664 |

A plot of Ln(Peroxide) versus time yielded a straight line with correlation coefficient $R^2=0.9796$, and equation, Ln(Peroxide)=−0.0013t+4.8932. The half-life=(Ln(2)/0.0013)=531.54 minutes=8.86 h.

The rate data indicate that different peroxy compounds are present in the allyl chloride samples studied. The peroxy compound or compounds present in the sample illustrated in Example 23A decomposed at about 20 times the rate of the ones in Example 23B. These data agree with the conclusion in Example 22 that more than one type of peroxy compound is present in allyl chloride. The different compounds are not necessarily present in the same proportions in all samples. Accordingly, a constant half-life was not obtained for the samples characterized.

Examples 24A-24E and 25

Examples 24A-24E and 25 illustrate the improvement in allyl chloride reactivity and CPTMS formation brought about by the addition of t-butylhydroperoxide and cumene hydroperoxide to an allyl chloride sample with unacceptable hydrosilylation performance. Its hydroperoxide concentration determined by QUANTOFIX® strips was 1-3 ppm and determined by iodometric titration was <4 ppm.

Each experiment was run with 13.15 g allyl chloride, 35 g trimethoxysilane and 32 µL ruthenium catalyst solution according to the procedure described above. RUCAT1 was used in Examples 24A-24E and RUCAT2 in Example 25. Tert-butyl hydroperoxide (TBHP) or cumene hydroperoxide (CUHP) in the amounts shown in Table 21 was added to the allyl chloride by syringe just prior to the hydrosilylation. Tert-butyl hydroperoxide was used as a 6M solution in decane.

Table 21 shows that the presence of tert-butyl hydroperoxide in the experiments of Examples 24B-24E led to complete allyl chloride consumption and increased formation of chloropropyltrimethoxysilane compared to the control (Example 24A) with no hydroperoxide additive. Improved hydrosilylation efficiency occurred within the 1000-6000 ppm tert-butyl hydroperoxide concentration range studied, but maximum product formation was observed between 1000-2000 ppm. When expressed as the peroxy functionality (—O—O—), the broad range studied was 35-2130 ppm and the optimum range was 355-710 ppm for the TBHP promoter.

The results of Example 25 show that cumene hydroperoxide is also an effective peroxy compound promoter of allyl chloride hydrosilylation by trimethoxysilane. Product formation was about 10 weight percent more than in the control (Example 24A) with the use of 238 ppm CUHP (equivalent to 50 ppm (—O—O—)) in the allyl chloride.

TABLE 21

Effects of t-Butylhydroperoxide (TBHP) and Cumene Hydro-peroxide (CUHP) on Allyl Chloride Hydrosilylation with Trimethoxysilane

| EXAMPLE | TBHP, ppm | TBHP, mmole | Unreacted Allyl Chloride, wt % | CPTMS, wt % |
|---|---|---|---|---|
| 24A | 0 | 0 | 11.36 | 80.65 |
| 24B | 180 | 0.028 | 0.00 | 88.93 |
| 24C | 1442 | 0.224 | 0.00 | 89.17 |
| 24D | 2884 | 0.448 | 0.00 | 88.41 |
| 24E | 5768 | 0.896 | 0.00 | 86.30 |

| EXAMPLE | CUHP, ppm | CUHP, mmole | Unreacted Allyl Chloride, wt % | CPTMS, wt % |
|---|---|---|---|---|
| 25 | 238 | 0.021 | 0.07 | 90.32 |

Examples 26-28

These Examples illustrate the improvements in allyl chloride hydrosilylation attendant to the use of the peroxy promoters, di-tert-butyl peroxide (DTBP), dicumyl peroxide (DICUP) and cumyl tert-butyl peroxide (CTBP). The allyl chloride used as raw material had earlier shown unacceptable hydrosilylation performance. Its hydroperoxide concentration determined by QUANTOFIX® strips was 1-3 ppm and determined by iodometric titration was <4 ppm. These Examples also show that peroxy compound concentration beyond an optimum range can lead to decreased formation of the hydrosilylation product.

DTBP, DICUP and CTBP were added to separate samples of allyl chloride to provide the range of peroxy compound concentrations listed in Table 22. Each experiment was done with 13.15 g allyl chloride, 35 g trimethoxysilane and 32 μL RUCAT2 according to the procedure described hereinabove. Results of the experiments are summarized in Table 22. DTBP, DICUP and CTBP concentrations shown in table are based on the weight of allyl chloride used. Peroxy (—O—O—) concentrations include the ~3 ppm present in the allyl chloride starting material. Allyl chloride and CPTMS values reported are for the reaction products free of excess TMS.

Comparison of the data of the following pairs, Examples 26A and 26B, Examples 27A and 27B and Examples 28A and 28B shows that CPTMS formation increased and residual allyl chloride decreased with the addition of 50 ppm DTBP, DICUP or CTBP to the allyl chloride starting material. Examples 26C and 26D illustrate maximum CPTMS formation with DTBP usage in the range, 100-400 ppm (equivalent to 24-90 ppm peroxide (—O—O—)). With DICUP, the maximum CPTMS formation occurred in Example 28E, wherein the peroxy compound usage was 400 ppm. Optimum DICUP concentration range was 200-500 ppm, which is equivalent to 23-65 ppm peroxide functionality (—O—O—).

TABLE 22

Data For Examples 26A-26E, 27A-27B And 28A-28F

| EXAMPLE | Peroxide, (—O—O—), ppm | Residual Allyl Chloride, wt % | CPTMS, wt % |
|---|---|---|---|
| DTBP, ppm | | | |
| 26A | 0 | ~3 | 11.08 | 81.53 |
| 26B | 50 | 13.96 | 8.20 | 83.65 |
| 26C | 100 | 24.92 | 0.00 | 91.86 |
| 26D | 300 | 68.75 | 1.52 | 90.72 |
| 26E | 500 | 112.59 | 4.89 | 85.53 |
| CTBP, ppm | | | |
| 27A | 0 | ~3 | 11.08 | 81.53 |
| 27B | 50 | 10.69 | 6.03 | 85.62 |
| DICUP, ppm | | | |
| 28A | 0 | ~3 | 11.08 | 81.53 |
| 28B | 50 | 8.93 | 7.54 | 84.77 |
| 28C | 100 | 14.85 | 4.51 | 87.31 |
| 28D | 200 | 26.70 | 3.89 | 87.99 |
| 28E | 400 | 50.41 | 1.34 | 90.38 |
| 28F | 600 | 74.11 | 6.57 | 85.19 |

Example 29A-29G

Examples 29A-G illustrate the utility of the peroxy ester, t-butyl peroxy-3,5,5-trimethylhexanoate, in promoting the hydrosilylation of allyl chloride by trimethoxysilane. One commercial source of the ester is TRIGONOX® 42S, a product of AKZO. The allyl chloride used as raw material had earlier shown unacceptable hydrosilylation performance. Its hydroperoxide concentration determined by QUANTOFIX® strips was 1-3 ppm and determined by iodometric titration was <4 ppm.

Six allyl chloride samples were prepared containing TRIGONOX® 42S in the range 365-8765 ppm. In each hydrosilylation experiment, the peroxy ester-promoted allyl chloride (13.8 g) was pumped into trimethoxysilane (35 g) containing 32 μL RUCAT2 following the general procedure already described above. The results summarized in Table 23 show that the peroxy ester, t-butyl peroxy-3,5,5-trimethylhexanoate (TRIGONOX® 42S) affords improved CPTMS formation over a wide concentration range. CPTMS was 94.49±0.16 wt % for TRIGONOX® 42S concentrations 350-6000 ppm in allyl chloride. The corresponding peroxy functionality concentration range is 45-786 ppm.

TABLE 23

Data For Examples 29A-29G

| EXAMPLE | TRIGONOX® 42S, ppm | EXOTHERM ° C. | *Residual Allyl Chloride, wt % | *CPTMS, wt % |
|---|---|---|---|---|
| 29A | 0 | 8.1 | 5.61 | 89.09 |
| 29B | 365.2 | 8.5 | 0.13 | 94.41 |
| 29C | 1460.9 | 9.2 | 0.15 | 94.63 |
| 29D | 2921.7 | 16.5 | 0.11 | 94.51 |
| 29E | 2921.7 | 16.4 | 0.11 | 94.66 |
| 29F | 5843.4 | 12.0 | 0.13 | 94.26 |
| 29G | 8765.2 | 8.2 | 0.30 | 92.26 |

*Allyl chloride and CPTMS values reported are for the reaction products free of excess TMS.

Example 30

Example 30 illustrates the use of compounds with peroxy functionality as promoters in the continuous hydrosilylation of allyl chloride with trimethoxysilane. The apparatus used was assembled in accordance with the disclosure in U.S. Pat. No. 6,015,920. It is described above and shown schematically in FIG. 1.

At the outset, the reactor was charged with 620 parts by weight of trimethoxysilane and 0.42 parts by weight ruthenium catalyst solution (RUCAT2) and heated to 75° C. RUCAT2 was saturated with 3% $O_2/N_2$ and this gas composition was also injected continuously into the reactor. Allyl chloride was dosed with di-tert-butyl peroxide (DTBP) so that the peroxy functionality (—O—O—) concentration was within the broad range, 10-100 ppm, and optimally 20-60 ppm, as determined by iodometric titration. The allyl chloride was then pumped into the reactor at the rate of 185 parts by weight per hour. An exotherm occurred and the reactor temperature was controlled between 85-90° C. GC analysis of the reaction mixture showed DTBP concentration was within the range, 15-60 ppm. The mixture in the reactor was kept agitated at 85-90° C. for 1-2 hours before it was discharged to the stripping column. Simultaneously, fresh trimethoxysilane, RUCAT2 and allyl chloride containing DTBP were pumped into the reactor at an overall rate that maintained both a steady-state liquid level in the reactor and a residence time of 1.5-2 hours. The gravimetric ratio of trimethoxysilane to allyl chloride was maintained in the range, 1.7-3.5.

The temperature of the reboiler in the stripping column was 175-190° C. The reaction mixture was separated into an overhead stream comprised mainly of TMS, which was recycled to the reactor inlet, and a crude product stream comprised mainly of CPTMS. The total of fresh and recycled TMS flow into the reactor was controlled at 620 parts by weight per hour. About 6000 parts by weight of crude product was collected after about 12 hours of continuous operation. Its composition is set forth in Table 24.

TABLE 24

Composition Of Crude CPTMS From Continuous Peroxide-Promoted Hydrosilylation Process

| COMPONENT | Wt % | COMPONENT | Wt % |
|---|---|---|---|
| Lower Boilers | 0.29 | $Cl(CH_2)_3Si(OCH_3)_3$ | 90.98 |
| Allyl Chloride | 0.61 | $ClSi(OCH_3)_3$ | 0.72 |
| $HSi(OCH_3)_3$ | 2.69 | $CH_3Si(OCH_3)_3$ | 0.13 |
| $Cl(CH_2)_3Si(OCH_3)_2Cl$ | 0.31 | $Si(OCH_3)_4$ | 1.42 |
| $(H_3CO)_3Si(CH_2)_3Si(OCH_3)_3$ | 0.25 | $C_3H_7Si(OCH_3)_3$ | 1.55 |
| $(H_3CO)_3Si(CH_2)_6Si(OCH_3)_3$ | 0.08 | High Boilers | 0.97 |

About 50-90 percent of the DTBP is decomposed during the hydrosilylation reaction and stripping operation. Most of the remainder exits the stripping column with the overhead TMS stream and is recycled to the reactor inlet. Accordingly, continuous or intermittent DTBP addition to the allyl chloride must occur to maintain the peroxy functionality concentration at effective levels. Other peroxy compounds with appropriate thermal and chemical stability can also be used in place of DTBP.

Example 31A-31C

These Examples illustrate the preparation and use of a phosphine-free ruthenium catalyst, wherein the ruthenium is fully in the Ru(II) oxidation state at outset of the hydrosilylation reaction. This Example also illustrates the need for effective peroxide levels when the Ru(II) catalyst composition is used for the hydrosilylation.

As has been mentioned above, commercial ruthenium trichloride is actually a 1:1 molar mixture of $RuCl_2$ and $RuCl_3$. Ru(III) was reduced to Ru(II) by the addition of 3 g powdered zinc to 10 ml of each of the methanolic solutions of ruthenium trichloride, described above as RUCAT1 and RUCAT2, and stirring the mixture in a nitrogen atmosphere until the zinc was completely reacted. Blue solutions indicating the presence of the anionic cluster, $[Ru_5Cl_{12}]^{2-}$, were obtained as expected from literature publications (See K M Frosin, et al., *Inorganica Chimica Acta*, vol 167 (1990) 83-89 and D. Rose, et al., *J Chem. Soc.* (A) 1970, pp 1791-1795).

ESR characterization of the blue solution from RUCAT 1 at 77 K showed g tensors at 2.49, 2.44 and 2.00 relative to DPPH at 2.0035. The spectrum was noticeably different from that of the original RUCAT 1. While Ru(II) has a formal $4d^6$ electronic configuration and is expected to be diamagnetic, Rose and Wilkinson (*J. Chem. Soc.* (A), 1970, pp 1792-1795) have also disclosed that the $[Ru_5Cl_{12}]^{2-}$ anion shows paramagnetism and yields an ESR spectrum with three g tensors.

The hydrosilylation reactions were done with 32 μL of the reduced RUCAT1 (Examples 31A and 31B) and 15 μL of the reduced RUCAT2 (Example 31C). Di-t-butylperoxide (DTBP 50 ppm) was added to the allyl chloride used in Example 31C for the experiment summarized in Example 31B.

TABLE 25

Ru(II)-Catalyzed Hydrosilylation of Allyl Chloride with $HSi(OCH_3)_3$

|  | EXAMPLE 31A | EXAMPLE 31B | EXAMPLE 31C |
|---|---|---|---|
| Total Peroxide in Allyl Chloride, ppm | 665 | 50 ppm DTBP | <4 |

TABLE 25-continued

Ru(II)-Catalyzed Hydrosilylation of Allyl Chloride with $HSi(OCH_3)_3$

|  | EXAMPLE 31A | EXAMPLE 31B | EXAMPLE 31C |
|---|---|---|---|
| Allyl Chloride, g | 13.4 | 13.4 | 13.4 |
| Trimethoxysilane, g | 35 | 35 | 35 |
| Ru(II) Solution, μL | 32 | 32 | 15 |
| DPM | No | No | Yes |
| Exotherm ° C. | 13.9 | 22.8 | 23.1 |
| Residual Allyl Chloride, wt % | 0.10 | 0.25 | 5.77 |
| TMS, wt % | 18.78 | 13.73 | 23.05 |
| TMOS, wt % | 6.07 | 10.73 | 11.51 |
| CPTMS, wt % | 75.05 | 75.29 | 59.66 |

The data for Examples 31A-31C show that divalent ruthenium, initially present as the anionic cluster, $[Ru_5Cl_{12}]^{2-}$, effected the hydrosilylation irrespective of the peroxide concentration of the allyl chloride. Hydrosilylation was incomplete in the experiment (Example 31C) wherein the peroxide concentration was less than 4 ppm. In separate additional experiments with the Ru(II) catalyst composition and allyl chloride used Example 31A, complete hydrosilylation was observed when 500 ppm tributyl phosphite was added to the allyl chloride. The yield of CPTMS was 88.96 wt %. However, 1000 ppm tributyl phosphite caused significant inhibition; CPTMS yield was only 55.63 wt %.

Example 32

This Example illustrates the peroxy-compound promotion of the hydrosilylation of methallyl chloride ($H_2C=C(CH_3)CH_2Cl$) by methyldimethoxysilane ($CH_3SiH(OCH_3)_2$). The peroxy compound is t-butylhydroperoxide (TBHP) and the ruthenium source is RUCAT 1.

The reaction is performed according to the Laboratory Reaction procedure described above. Methyldimethoxysilane (49.3 g, 0.46 mole) and 32 μL RUCAT 1 are placed in the flask and heated to 58° C. Methallyl chloride (21.9 g, 0.29 mole) containing 0.024 g TBHP is added at about 0.2 g/min, during which the temperature increases to 70° C. Following the addition, the reaction temperature is increased to 80° C. and the reaction mixture is left stirring overnight. GC/MS analysis shows that the reaction product is 3-chloro-2-methylpropyl(methyldimethoxysilane), which by GC analysis accounts for 60 wt % of the reaction mixture.

Example 33

This Example illustrates the peroxy-compound promotion of the hydrosilylation of allyl chloride ($H_2C=CHCH_2Cl$) by triethoxysilane ($HSi(OC_2H_5)_3$). The peroxy compound is di-t-butylperoxide (DTBP) and the ruthenium source is zinc-reduced RUCAT 1 prepared as described in Example 31. Zinc-reduced RUCAT 1 contains $[Ru_5Cl_{12}]^{2-}$ anion in which Ru is present as Ru(II). Triethoxysilane is distilled product obtained via the Direct Process disclosed in U.S. Pat. No. 7,429,672 and has toluene content less than 150 ppm.

The reaction is performed according to the Laboratory Reaction procedure described above. Triethoxysilane (47.3 g, 0.29 mole) and 32 μL Zn-reduced RUCAT 1 are placed in the flask and heated to 80° C. Allyl chloride (14.0 g, 0.18 mole) containing 1.4 mg DTBP is added at about 0.3 g/min, during which the temperature increases to 91° C. The reaction mixture is maintained at 85-90° C. for 4 hours.

GC/MS analysis shows that the reaction product is 3-chloropropyltriethoxysilane, which by GC analysis accounts for 65 wt % of the reaction mixture.

Example 34

This Example illustrates the peroxy-compound promotion of the hydrosilylation of methallyl chloride ($H_2C$=$C(CH_3)CH_2Cl$) by trimethoxysilane ($HSi(OCH_3)_3$). The peroxy compound is the peroxy ester, t-butyl peroxy-3,5,5-trimethylhexanoate (Trigonox® 4S) and the ruthenium source is RUCAT 1.

The reaction is performed according to the Laboratory Reaction procedure described above. Trimethoxysilane (56.1 g, 0.46 mole) and 32 μL RUCAT 1 are placed in the flask and heated to 75° C. Methallyl chloride (22.0 g, 0.29 mole) containing 0.10 g Trigonox® 4S is added at about 0.2 g/min, during which the temperature increases to 85° C. Reaction is kept stirring at 95° C. for twelve hours. GC/MS analysis shows that the reaction product is 3-chloro-2-methylpropyltrimethoxysilane, which by GC analysis accounts for 64 wt % of the reaction mixture.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto. All patents, patent applications, and references cited are herein incorporated by reference in their entireties.

What is claimed is:

1. A process for producing a haloorganoalkoxysilane product of Formula (I),

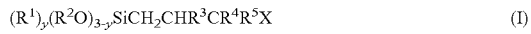

$(R^1)_y(R^2O)_{3-y}SiCH_2CHR^3CR^4R^5X$  (I)

comprising reacting at a temperature of from about 50° C. to about 130° C.
(a) an olefinic halide having the formula $H_2C$=$CR^3CR^4R^5X$;
(b) an alkoxysilane having the formula $(R^1)_y(R^2O)_{3-y}SiH$;
(c) a catalytically effective amount of ruthenium-containing catalyst; and
(d) a reaction-promoting effective amount of a peroxy compound selected from the group consisting of (i) a hydroperoxide having a decomposition rate with a half-life of 1 hour at a temperature of from 30° C. to 200° C., (ii) a Group 14 hydroperoxide having a decomposition rate with a half-life of 1 hour at a temperature of from 30° C. to 200° C., (iii) a Group 14 peroxide having a decomposition rate with a half-life of 1 hour at a temperature of from 30° C. to 200° C., (iv) a ketone peroxide having a decomposition rate with a half-life of 1 hour at a temperature of from 30° C. to 200° C., (v) a peroxide having the general formula R—O—O—R, wherein R is a C1 to C25 group that is linear or branched, saturated or unsaturated, cyclic, aromatic or alkaryl and having a decomposition rate with a half-life of 1 hour at a temperature of from 100° C. to 160° C., (vi) a diacyl peroxide having a decomposition rate with a half-life of 1 hour at a temperature of from 40° C. to 100° C., (vii) a peroxy dicarbonate having a decomposition rate with a half-life of 1 hour at a temperature of from 50° C. to 75° C., (viii) a peroxy ester having a decomposition rate with a half-life of 1 hour at a temperature of from 50° C. to 100° C. and (ix) a peroxy ketal having a decomposition rate with a half-life of 1 hour at a temperature of from 100° C. to 150° C., provided, where any of peroxy compounds (i)-(ix) contains a cyclic group, such group is monocyclic, optionally in the presence of an electron-donating aromatic compound, to produce the haloorganoalkoxysilane product,
wherein
$R^1$ and $R^2$ are alkyl groups of from 1 to 6 carbon atoms;
$R^3$ is an alkyl group of from 1 to 6 carbon atoms or hydrogen;
$R^4$ is an alkyl group of from 1 to 6 carbon atoms, hydrogen or halogen;
$R^5$ is hydrogen or an alkyl group of from 1 to 6 carbon atoms;
X is a halogen; and
y is 0,1 or 2; and, wherein the peroxy compound (d) is pre-mixed with the olefinic halide (a).

2. The process of claim 1, wherein the olefinic halide is selected from the group consisting of allyl chloride, methallyl chloride, 3-chloro-1-butene, 3,4-dichloro-1-butene, 2-chloropropene, and combinations thereof.

3. The process of claim 1, wherein said alkoxysilane is selected from the group consisting of trimethoxysilane, methyldimethoxysilane, dimethylmethoxysilane, triethoxysilane, methyldiethoxysilane, dimethylethoxysilane, ethyldiethoxysilane, dicthylethoxysilane, and combinations thereof.

4. The process of claim 1, wherein said reaction-promoting effective amount of said peroxy compound ranges from about 1 to about 2000 ppm, based on the total weight of the reaction mass.

5. The process of claim 1, wherein said reaction-promoting effective amount of said peroxy compound is from 350 to 6000 ppm for t-butylperoxy-3,5,5-trimethylhexanoate, from 20 to 100 ppm for allyl hydroperoxide, from 50 to 1000 ppm for t-butyl hydroperoxide, from 50 to 1000 ppm for cumene hydroperoxide, from 3 to 300 ppm for di-tert-butyl peroxide, from 50 to 1000 ppm for dicumyl peroxide, from 50 to 2500 ppm for dibenzoyl peroxide, from 50 to 3500 ppm for di(n-peropyl)peroxydicarbonate or from 50 to 3500 ppm for di(2-ethylhexyl)peroxydicarbonate, based on the total weight of the reaction mass.

6. The process of claim 1, wherein said hydroperoxides(i) and (ii) have the formula R—O—O—H or $R_2C(O$—O—$H)_2$, wherein R is a C1 to C25 group that is linear or branched, saturated or unsaturated, cyclic, aromatic or alkaryl.

7. The process of claim 6, wherein said hydroperoxides (i) and (ii) are selected from the group consisting of t-butyl hydroperoxide, t-amyl hydroperoxide, cumene hydroperoxide, allyl hydroperoxide, tetrahydrofuryl hydroperoxide, limonene hydroperoxides, terpene hydroperoxides, steroidal hydroperoxides, 2,5-dihydroperoxy-2,5-dimethylhexane, and combinations thereof.

8. The process of claim 1, wherein said Group 14 hydroperoxides (ii) and Group 14 peroxides (iii) have the formula Z—O—O—H, wherein Z is a silyl, germyl or stannyl moiety.

9. The process of claim 8, wherein said Group 14 hydroperoxides (ii) and Group 14 peroxides (iii) are selected from the group consisting of trimethylsilylhydroperoxide, tribenzylsilylhydro-peroxide, tert-butyldimethylsilylhydroperoxide, methyldiphenylsilylhydroperoxide, triphenylsilyihydroperoxide, and combinations thereof.

10. The process of claim 1, wherein said peroxides (v) are selected from the group consisting of di-t-butyl peroxide, di-t-amyl peroxide, dicumyl peroxide, 2,5-dimethyl-2,5-di(t-butylperoxy)hexane, and combinations thereof.

11. The process of claim 1, wherein said diacyl peroxides (vi) have the general formula $(RC(O)O)_2$, wherein R is a linear or branched, cyclic, aromatic or alkaryl group having 1-25 carbon atoms.

12. The process of claim 11, wherein said diacyl peroxides (vi) are selected from the group consisting of didecanoyl peroxide, dilauroyl peroxide, dibenzoyl peroxide, and combinations thereof.

13. The process of claim 1, wherein said peroxy esters (viii) have the general formula, RC(O)O—OR, wherein each occurrence of R is a linear or branched, cyclic, aromatic or alkaryl group containing 1-25 carbon atoms.

14. The process of claim 13, wherein said peroxy esters (viii) are selected from the group consisting of cumyl peroxyneodecanoate, t-amyl peroxypivalate, t-butyl peroxy-3,5,5-trimethylhexanoate, and combinations thereof.

15. The process of claim 1, wherein said peroxy dicarbonates (vii) have the general formula $(ROC(O)O)_2$, wherein R is a linear or branched, cyclic, aromatic or alkaryl group containing 1-25 carbon atoms.

16. The process of claim 15, wherein said peroxy dicarbonates (vii) are selected from the group consisting of di(n-propyl)peroxydicarbonate, di(2-ethylhexyl)peroxydicarbonate, and combinations thereof.

17. The process of claim 1, wherein said peroxy ketals (ix) have the general formula, $R_2C(O$—$O$—$R')_2$, wherein R and R' are each individually linear or branched, cyclic, aromatic or alkaryl groups containing 1-25 carbon atoms.

18. The process of claim 17, wherein said peroxy ketals (ix) are selected from the group consisting of ethyl-3,3-di(t-butylperoxy)butyrate, 1,1-di(t-butylperoxy)cyclohexane, 1,1-di(t-butyl-peroxy)3,3,5-trimethylcyclohexane, and combinations thereof.

19. The process of claim 1, wherein said ruthenium-containing catalyst is selected from the group consisting of particulate ruthenium, ruthenium halides, zinc-reduced or tin reduced reaction products of ruthenium halides, cycloolefin complexes of ruthenium, amine complexes of ruthenium, and combinations thereof.

20. The process of claim 19, wherein said ruthenium-containing catalyst is selected from the group consisting of $RuCl_3$, $RuBr_3$, $MRuCl_3$, $M_2Ru_5Cl_{12}$, $M_4Ru_4Cl_{12}$, where M=H, or alkali metal; $ZnRu_5Cl_{12}$ and $SnRu_5Cl_{12}$; $RuO_2$, $Ru_3(CO)_{12}$, $[Ru(CO)_3Cl_2]_2$; cycloolefin complexes of ruthenium Ru(COD)(COT), COD—$RuCl_2$, [COD—$RuCl_2$] where COD is cyclooctadiene and COT is cyclooctatriene; bis(6,6-dimethylcyclopentadienyl)ruthenium, bis($\eta^5$-2,4-dimethylpentadienyl)ruthenium, bis(1,3-dimethylcyclopentadienyl)ruthenium Ru(AcAc)$_3$ where AcAc is an acetylacetonate ligand; ($\pi$-arene) ruthenium complexes such as (p-cymene) ruthenium (II) chloride dimer and (benzene) ruthenium (II) chloride dimer, $[Ru(NH_3)_6]X_2$ and $[Ru(NH_3)_6]X_3$ where X is a halogen; and, combinations thereof.

21. The process of claim 1, wherein said electron-donating aromatic compound is selected from the group consisting of benzene, ethylbenzene, diethylbenzene, triethylbenzene, $\eta$-butylbenzene, di-t-butylbenzene, bibenzyl, toluene, t-butyltoluene, anisole, 1-phenylhexane, 1-phenyldodecane, mixtures of n-alkylbenzenes with alkyl groups of from $C_8$ to $C_{20}$, mixtures of diphenylalkanes and bibenzyl isomers, mixtures of benzyl toluenes and dibenzyl toluenes, m-xylene, mesitylene, p-cymene, diphenylmethane, triphenylmethane, phenyl ether, phenothiazine, biphenyl, and combinations thereof.

22. The process of claim 1, wherein component (b) is present in said process in molar excess relative to component (a).

23. The process of claim 1, wherein said ruthenium-containing catalyst is substantially-free of phosphine.

24. The process of claim 1, wherein component (a) is allyl chloride, component (b) is trimethoxysilane, component (c) is $RuCl_3$, and component (d) is di(t-butyl)peroxide.

25. The process of claim 1, wherein said ruthenium-containing catalyst is a zinc-reduced reaction products of ruthenium halides or tin reduced reaction products of ruthenium halides.

26. The process of claim 1, wherein the ruthenium-containing catalyst (c) is sparged with oxygen before contact of the catalyst (c) with the peroxy compound (d).

* * * * *